US012697496B2

(12) United States Patent
Ries et al.

(10) Patent No.: US 12,697,496 B2
(45) Date of Patent: Aug. 4, 2026

(54) FEEDTHROUGH ASSEMBLY AND IMPLANTABLE MEDICAL DEVICE INCLUDING SAME

(71) Applicant: Medtronic, Inc., Minneapolis, MN (US)

(72) Inventors: Andrew J. Ries, Lino Lakes, MN (US); Mark E. Henschel, Phoenix, AZ (US); James R. Wasson, Tempe, AZ (US); Chunho Kim, Phoenix, AZ (US); Walter E. Benecke, Scottsdale, AZ (US); Kris A. Peterson, Edina, MN (US); Jeff M. Wheeler, Gilbert, AZ (US); Songhua Shi, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 775 days.

(21) Appl. No.: 18/102,367

(22) Filed: Jan. 27, 2023

(65) Prior Publication Data

US 2023/0248982 A1      Aug. 10, 2023

Related U.S. Application Data

(60) Provisional application No. 63/307,768, filed on Feb. 8, 2022.

(51) Int. Cl.
*A61N 1/00* (2006.01)
*A61N 1/372* (2006.01)
*A61N 1/375* (2006.01)

(52) U.S. Cl.
CPC ....... *A61N 1/3754* (2013.01); *A61N 1/37223* (2013.01)

(58) Field of Classification Search
None
See application file for complete search history.

(56) References Cited

U.S. PATENT DOCUMENTS

| | | | |
|---|---|---|---|
| 8,162,684 | B1 | 4/2012 | Sochor |
| 10,124,559 | B2 | 11/2018 | Sandlin et al. |
| 2006/0247711 | A1 | 11/2006 | Verhoef et al. |
| 2015/0321012 | A1 | 11/2015 | Cinbis et al. |

(Continued)

OTHER PUBLICATIONS

International Search Report and Written Opinion for PCT/IB2023/050924 dated Mar. 27, 2023 (10 pages).

(Continued)

*Primary Examiner* — William J Levicky
*Assistant Examiner* — Anant A Gupta
(74) *Attorney, Agent, or Firm* — Mueting Raasch Group

(57) ABSTRACT

Various embodiments of a feedthrough assembly are disclosed. The assembly includes a header and a test fanout layer electrically connected to the header. A first major surface of the test fanout layer faces an inner surface of the header. The assembly further includes a test via extending between the first major surface and a second major surface of the test fanout layer, and a test pad disposed on the first major surface of the test fanout layer and electrically connected to the test via. At least a portion of the test pad is disposed between the outer surface of the header and a perimeter of the test fanout layer as viewed in a plane parallel to the first major surface of the test fanout layer such that the at least a portion of the test pad is exposed.

20 Claims, 12 Drawing Sheets

(56)        References Cited

U.S. PATENT DOCUMENTS

| | | | |
|---|---|---|---|
| 2016/0184593 A1 | 6/2016 | Ruben et al. | |
| 2016/0192524 A1* | 6/2016 | Ruben | H05K 5/066 |
| | | | 361/728 |
| 2018/0304084 A1 | 10/2018 | Stevenson et al. | |
| 2019/0030346 A1* | 1/2019 | Li | A61N 1/3702 |
| 2019/0184179 A1 | 6/2019 | Stahmann et al. | |
| 2020/0155860 A1 | 5/2020 | Keller et al. | |
| 2021/0178518 A1 | 6/2021 | Ruben et al. | |
| 2021/0187307 A1 | 6/2021 | Ries et al. | |
| 2021/0220657 A1 | 7/2021 | Villavicencio et al. | |
| 2021/0228888 A1 | 7/2021 | Zhang et al. | |

OTHER PUBLICATIONS

U.S. Appl. No. 17/071,463, filed Oct. 15, 2020.
U.S. Appl. No. 17/118,283, filed Dec. 10, 2020.

* cited by examiner

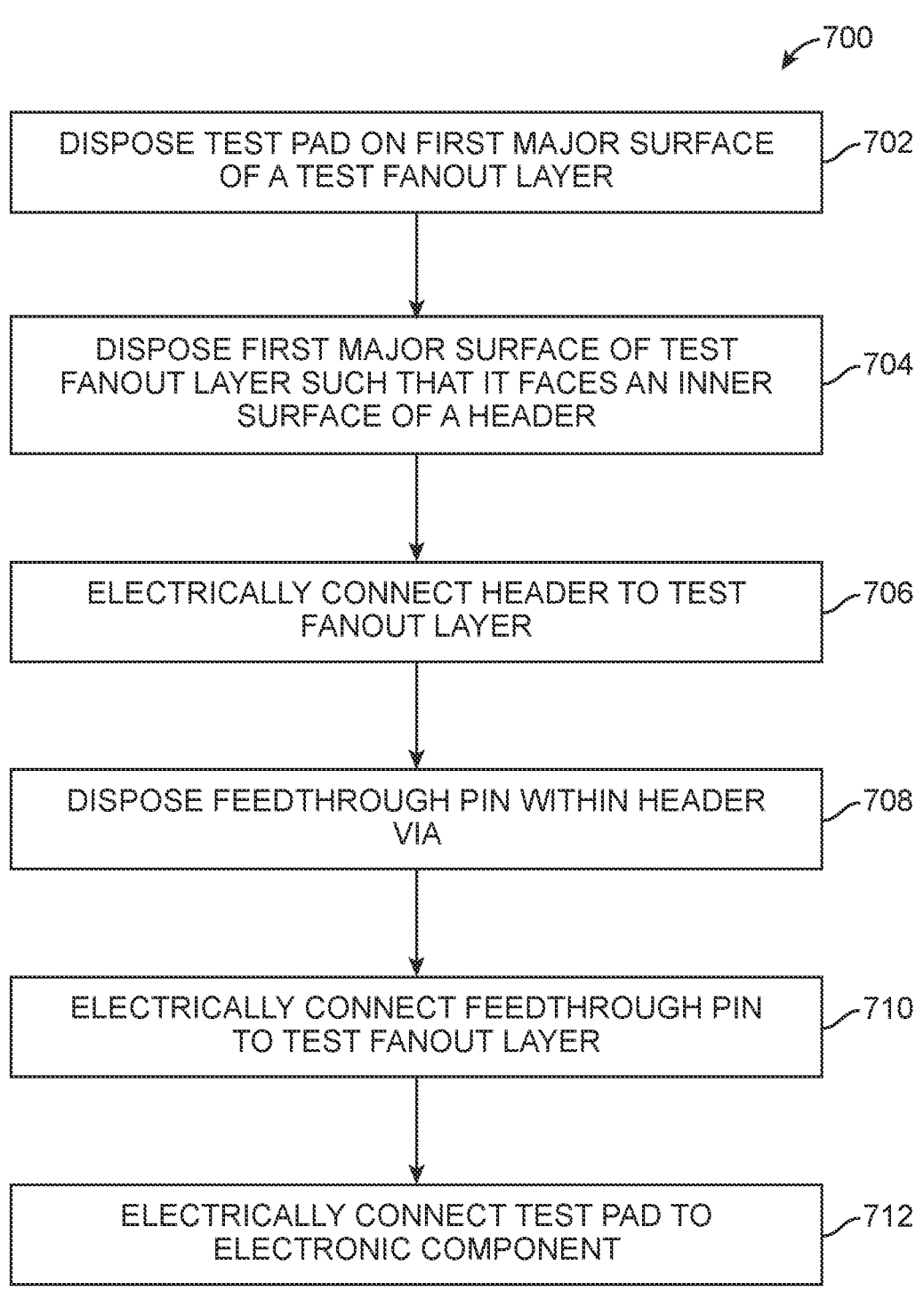

700

DISPOSE TEST PAD ON FIRST MAJOR SURFACE OF A TEST FANOUT LAYER — 702

DISPOSE FIRST MAJOR SURFACE OF TEST FANOUT LAYER SUCH THAT IT FACES AN INNER SURFACE OF A HEADER — 704

ELECTRICALLY CONNECT HEADER TO TEST FANOUT LAYER — 706

DISPOSE FEEDTHROUGH PIN WITHIN HEADER VIA — 708

ELECTRICALLY CONNECT FEEDTHROUGH PIN TO TEST FANOUT LAYER — 710

ELECTRICALLY CONNECT TEST PAD TO ELECTRONIC COMPONENT — 712

FIG. 19

FEEDTHROUGH ASSEMBLY AND IMPLANTABLE MEDICAL DEVICE INCLUDING SAME

CROSS-REFERENCE TO RELATED APPLICATION

This application claims the benefit of U.S. Provisional Application No. 63/307,768, filed Feb. 8, 2022, the disclosure of which is incorporated by reference herein in its entirety.

TECHNICAL FIELD

This disclosure generally relates to a feedthrough assembly and in particular to an implantable medical device that includes the feedthrough assembly.

BACKGROUND

Implantable medical devices such as an implantable pacemaker can deliver pacing pulses to a patient's heart and monitor conditions of the patient's heart. In some examples, the implantable pacemaker includes a pulse generator and one or more electrical leads. The pulse generator may, for example, be implanted in a small pocket in the patient's chest. The electrical leads can be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the distal ends of the electrical leads are positioned at the target site. The pulse generator may provide electrical stimulation to the target site and/or monitor cardiac electrical activity at the target site via the electrodes.

Other implantable pacemakers are configured to be implanted entirely within a chamber of the heart. Such pacemakers can be referred to as intracardiac pacing devices or leadless pacing devices and can include one or more electrodes on their outer housings to deliver therapeutic electrical signals and/or sense intrinsic depolarizations of the heart. Such pacemakers can be positioned within or outside of the heart and, in some examples, can be anchored to a wall of the heart via a fixation mechanism.

SUMMARY

The techniques of this disclosure generally relate to feedthrough assembly that includes a test fanout layer electrically connected to a header. The test fanout layer can include one or more test pads that are disposed on a first major surface of the test fanout layer that faces an inner surface of the header. At least one of the test pads can be electrically connected to an electronic component disposed on or within an electronic layer that faces a second major surface of the test fanout layer. The test pad can be adapted to allow for testing of the electronic component after the header, test fanout layer, and electronic layer have been connected.

This disclosure includes without limitation the following clauses:

Clause 1: A feedthrough assembly that includes a header having an inner surface and an outer surface, and a test fanout layer electrically connected to the header. The test fanout layer includes a first major surface, a second major surface, and a perimeter, where the first major surface of the test fanout layer faces the inner surface of the header; a test via extending between the first major surface and the second major surface of the test fanout layer; and a test pad disposed on the first major surface of the test fanout layer and electrically connected to the test via, where at least a portion of the test pad is disposed between the outer surface of the header and the perimeter of the test fanout layer as viewed in a plane parallel to the first major surface of the test fanout layer such that the at least a portion of the test pad is exposed.

Clause 2: The assembly of clause 1, further including a first feedthrough pin disposed within a first header via that extends through the header, where the first feedthrough pin extends outward beyond the outer surface of the header.

Clause 3: The assembly of clause 2, where the first feedthrough pin extends into a metallized through hole that extends between the first major surface and the second major surface of the test fanout layer such that the first feedthrough pin is electrically connected to the metallized through hole.

Clause 4: The assembly of clause 3, where the first feedthrough pin extends through the metallized through hole and beyond the second major surface of the test fanout layer.

Clause 5: The assembly of clause 2, further including a redistribution layer disposed between the header and the test fanout layer, where the test fanout layer and the first feedthrough pin are electrically connected to the header utilizing the redistribution layer.

Clause 6: The assembly of clause 2, further including conductive pads disposed on the inner surface of the header and the first feedthrough pin, where the test fanout layer is electrically connected to the header and first feedthrough pin utilizing the conductive pads.

Clause 7: The assembly of any one of clauses 2-6, further including a second feedthrough pin disposed within a second header via that extends through the header, where the second feedthrough pin extends outward beyond the outer surface of the header.

Clause 8: The assembly of any one of clauses 2-7, further including insulating material disposed between the first feedthrough pin and at least a portion of the via disposed through the header such that the first feedthrough pin is electrically isolated from the header.

Clause 9: The assembly of any one of clauses 1-8, further including an electronic component disposed on or within the test fanout layer and electrically connected to the header.

Clause 10: The assembly of clause 9, where the electronic component includes at least one of a filter, capacitor, or diode.

Clause 11: The assembly of any one of clauses 9-10, where the test pad is electrically connected to the electronic component.

Clause 12: The assembly of any one of clauses 9-11, where the electronic component is disposed on the second major surface of the test fanout layer.

Clause 13: The assembly of any one of clauses 1-12, where a post disposed on the inner surface of the header is electrically connected to a metallized through hole of the test fanout layer.

Clause 14: The assembly of any one of clauses 1-12, where the header is electrically connected to the test fanout layer by a patterned conductive layer disposed on the first major surface of the test fanout layer, where the patterned conductive layer includes a first conductive portion and a second conductive portion electrically isolated from the first conductive portion.

Clause 15: The assembly of clause 14, where the first conductive portion is electrically connected to the header by a conductive post that extends from the inner surface of the header.

Clause 16: The assembly of any one of clauses 14-15, where the feedthrough pin is electrically connected to the second conductive portion of the patterned conductive layer.

Clause 17: The assembly of clause 16, where the feedthrough pin extends through the second conductive portion of the patterned conductive layer.

Clause 18: The assembly of any one of clauses 1-17, further including an adhesive layer disposed between the inner surface of the header and the test fanout layer.

Clause 19: The assembly of clause 18, where the adhesive layer includes an anisotropic conductive adhesive layer that is adapted to electrically connect the header to the first conductive portion of the patterned conductive layer and the feedthrough pin to the second conductive portion of the patterned conductive layer.

Clause 20: The assembly of any one of clauses 1-19, further including a tissue fixation component connected to the header.

Clause 21: The assembly of clause 20, where the tissue fixation component is electrically connected to the header.

Clause 22: The assembly of any one of clauses 20-21, where the tissue fixation component includes at least one of a tine or helix.

Clause 23: The assembly of any one of clauses 1-22, where the header is adapted to be electrically and mechanically connected to an end cap that is disposed over the header.

Clause 24: The assembly of any one of clauses 1-23, further including a plurality of test pads disposed on the test fanout layer, where each test pad of the plurality of test pads is electrically connected to a test via that extends between the first major surface and the second major surface of the test fanout layer.

Clause 25: The assembly of any one of clauses 1-24, where the assembly extends along a longitudinal axis such that the first and second major surfaces of the test fanout layer are substantially orthogonal to the longitudinal axis, and further where a normal to the test pad is substantially parallel to the longitudinal axis.

Clause 26: An electronics module that includes an electronic layer having a substrate and an electronic component disposed on the substrate, and a feedthrough assembly electrically connected to the electronic layer. The feedthrough assembly includes a header having an inner surface and an outer surface, and a test fanout layer electrically connected to the header. The test fanout layer includes a first major surface, a second major surface, and a perimeter, where the first major surface of the test fanout layer faces the inner surface of the header; and a test pad disposed on the first major surface of the test fanout layer and electrically connected to the electronic component of the electronic layer, where at least a portion of the test pad is disposed between the outer surface of the header and the perimeter of the test fanout layer as viewed in a plane parallel to the first major surface of the test fanout layer such that the at least a portion of the test pad is exposed.

Clause 27: The module of clause 26, further including a test via that extends between the first major surface and the second major surface of the test fanout layer, where the test via electrically connects the test pad to the electronic component.

Clause 28: The module of any one of clauses 26-27, where the test fanout layer further includes a second test pad disposed on the first major surface of the test fanout layer, where at least a portion of the second test pad is disposed between the outer surface of the header and the perimeter of the test fanout layer as viewed in a plane parallel to the first major surface of the test fanout layer such that the at least a portion of the second test pad is exposed.

Clause 29: The module of clause 28, where the second test pad is electrically connected to a second electronic component of the electronic layer.

Clause 30: The module of clause 29, further including a second test via that extends between the first major surface and the second major surface of the test fanout layer, where the second test via electrically connects the second test pad to the second electronic component of the electronic layer.

Clause 31: The module of any one of clauses 26-30, where the feedthrough assembly further includes a feedthrough pin disposed within a via that extends through the header, wherein the feedthrough pin extends beyond the outer surface of the header.

Clause 32: The module of clause 31, where the feedthrough pin is electrically connected to a metallized through hole that extends between the first major surface and the second major surface of the test fanout layer such that the feedthrough pin is electrically connected to the metallized through hole.

Clause 33: The module of clause 32, where the first feedthrough pin extends through the metallized through hole and beyond the second major surface of the test fanout layer.

Clause 34: The module of clause 31, further including a redistribution layer disposed between the header and the test fanout layer, where the fanout layer and the first feedthrough pin are electrically connected to the header utilizing the redistribution layer.

Clause 35: The module of clause 31, further including conductive pads disposed on the inner surface of the header and the first feedthrough pin, where the test fanout layer and the first feedthrough pin are electrically connected to the header utilizing the conductive pads.

Clause 36: The module of any one of clauses 31-35, where the feedthrough assembly further includes a second feedthrough pin disposed within a second via of the header that extends through the header, where the second feedthrough pin extends beyond the outer surface of the header.

Clause 37: The module of any one of clauses 31-38, where the feedthrough assembly further includes insulating material disposed between the feedthrough pin and at least a portion of the via disposed through the header such that the feedthrough pin is electrically isolated from the header.

Clause 38: The module of any one of clauses 26-37, where the feedthrough assembly further includes an electronic component disposed on or within the test fanout layer and electrically connected to the header.

Clause 39: The module of clause 38, where the electronic component of the test fanout layer includes at least one of a filter, capacitor, or diode.

Clause 40: The module of any one of clauses 26-39, where a post disposed on the inner surface of the header extends through the test fanout layer and electrically connects the header to the electronic layer.

Clause 41: The module of any one of clauses 26-40, where the feedthrough assembly further includes a patterned conductive layer disposed on the first major surface of the test fanout layer, where the patterned conductive layer includes a first conductive portion and a second conductive portion electrically isolated from the first conductive portion.

Clause 42: The module of clause 41, where the first conductive portion is electrically connected to the header by a conductive post that extends from the inner surface of the header.

Clause 43: The module of any one of clauses 41-42, where the feedthrough pin is electrically connected to the second conductive portion of the patterned conductive layer.

Clause 44: The module of clause 43, where the feedthrough pin extends through the second conductive portion of the patterned conductive layer.

Clause 45: The module of any one of clauses 26-44, further including an adhesive layer disposed between the inner surface of the header and the test fanout layer.

Clause 46: The module of clause 45, where the adhesive layer includes an anisotropic conductive adhesive layer that is adapted to electrically connect the header to the first conductive portion of the patterned conductive layer and the feedthrough pin to the second conductive portion of the patterned conductive layer.

Clause 47: The module of any one of clauses 26-46, further including a tissue fixation component connected to the header.

Clause 48: The module of clause 47, where the tissue fixation component is electrically connected to the header.

Clause 49: The module of any one of clauses 47-48, where the tissue fixation component comprises at least one of a tine or helix.

Clause 50: The module of any one of clauses 26-49, where the header is adapted to be electrically and mechanically connected to an end cap.

Clause 51: The module of any one of clauses 26-50, further including a plurality of test pads disposed on the test fanout layer, where each test pad of the plurality of test pads is electrically connected to a test via that extends between the first major surface and the second major surface of the test fanout layer.

Clause 52: The module of any one of clauses 26-51, where the module extends along a longitudinal axis such that the first and second major surfaces of the test fanout layer are substantially orthogonal to the longitudinal axis, and further where a normal to the test pad is substantially parallel to the longitudinal axis.

Clause 53: An implantable medical device including a power source; and an electronics module electrically connected to the power source and including an electronic layer and a feedthrough assembly electrically connected to the electronic layer, where the electronic layer includes a substrate and an electronic component disposed on the substrate. The feedthrough assembly includes a header having an inner surface and an outer surface and a test fanout layer electrically connected to the header. The test fanout layer includes a first major surface, a second major surface, and a perimeter, where the first major surface of the test fanout layer faces the inner surface of the header; and a test pad disposed on the first major surface of the test fanout layer and electrically connected to the electronic component of the electronic layer, where at least a portion of the test pad is disposed between the outer surface of the header and the perimeter of the test fanout layer as viewed in a plane parallel to the first major surface of the test fanout layer such that the at least a portion of the test pad is exposed.

Clause 54: The device of clause 53, further including a test via that extends between the first major surface and the second major surface of the test fanout layer, where the test via electrically connects the test pad to the electronic component of the electronic layer.

Clause 55: The device of any one of clauses 53-54, further including an elongated tubular housing extending between a first end and a second end along a longitudinal axis, and further where a first portion of the housing adjacent to the first end encloses the electronics module and a second portion of the housing adjacent to the second end encloses the power source.

Clause 56: The device of clause 55, where the first portion of the elongated tubular housing includes a substantially transparent material.

Clause 57: The device of any one of clauses 53-56, where the longitudinal axis is substantially orthogonal to the test fanout layer of the feedthrough assembly.

Clause 58: The device of any one of clauses 53-57, where the longitudinal axis is substantially orthogonal to the substrate of the electronic layer of the electronics module.

Clause 59: The device of any one of clauses 53-58, further including a feedthrough pin disposed within a via that extends through the header, where the feedthrough pin extends beyond the outer surface of the header.

Clause 60: The device of clause 59, where the feedthrough pin is electrically connected to a metallized through hole that extends between the first major surface and the second major surface of the test fanout layer such that the feedthrough pin is electrically connected to the metallized through hole.

Clause 61: The device of clause 60, where the first feedthrough pin extends through the metallized through hole and beyond the second major surface of the test fanout layer.

Clause 62: The device of clause 59, further including a redistribution layer disposed between the header and the test fanout layer, where the fanout layer and the first feedthrough pin are electrically connected to the header utilizing the redistribution layer.

Clause 63: The device of clause 59, further including conductive pads disposed on the inner surface of the header and the first feedthrough pin, where the fanout layer and the first feedthrough pin are electrically connected to the header utilizing the conductive pads.

Clause 64: The device of any one of clauses 59-63, further including a second feedthrough pin disposed within a second via that extends through the header, where the second feedthrough pin extends beyond the outer surface of the header.

Clause 65: The device of any one of clauses 53-64, further including a tissue fixation component connected to the header.

Clause 66: The device of clause 65, where the tissue fixation component is electrically connected to the header.

Clause 67: The device of any one of clauses 65-66, where the tissue fixation component includes at least one of a tine or helix.

Clause 68: The device of any one of clauses 53-67, where the header is adapted to be electrically and mechanically connected to an end cap.

Clause 69: The device of any one of clauses 53-68, further including a plurality of test pads disposed on the test fanout layer, where each test pad of the plurality of test pads is electrically connected to a test via that extends between the first major surface and the second major surface of the test fanout layer.

Clause 70: The device of any one of clauses 53-69, where the assembly extends along a longitudinal axis such that the first and second major surfaces of the test fanout layer are substantially orthogonal to the longitudinal axis, and further where a normal to the test pad is substantially parallel to the longitudinal axis.

Clause 71: A method including disposing a test pad on a first major surface of a test fanout layer; disposing the first major surface of the test fanout layer such that it faces an inner surface of a header and such that at least a portion of the test pad is disposed between an outer surface of the header and a perimeter of the test fanout layer when viewed in a plane parallel to the first major surface of the test fanout layer, where the at least a portion of the test pad is exposed; and electrically connecting the header to the test fanout layer. The method further includes disposing a feedthrough pin within a header via that extends through the header, where the feedthrough pin extends outward beyond an outer surface of the header; electrically connecting the feedthrough pin to the test fanout layer; and electrically connecting the test pad to an electronic component disposed on a substrate of an electronic layer disposed such that it faces a second major surface of the test fanout layer.

Clause 72: The method of clause 71, further including disposing a test via in the test fanout layer such that it extends between the first major surface and a second major surface of the test fanout layer, and electrically connecting the test pad to the test via.

Clause 73: The method of any one of clauses 71-72, further including disposing one or more electronic components on or within the test fanout layer.

Clause 74: The method of any one of clauses 71-73, further including disposing a patterned conductive layer on the first major surface of the test fanout layer, where the patterned conductive layer includes a first conductive portion and a second conductive portion.

Clause 75: The method of clause 74, further including electrically connecting the header to the first conductive portion of the patterned conductive layer.

Clause 76: The method of any one of clauses 74-75, further including electrically connecting the second conductive portion of the patterned conductive layer to the electronic component of the electronic layer.

Clause 77: The method of any one of clauses 71-76, further including connecting the header to a first end of a housing such that the electronic layer is disposed within the housing, and electrically connecting a power source to the electronic layer.

Clause 78: The method of any one of clauses 71-76, where electrically connecting the header to the test fanout layer includes disposing an adhesive layer between the inner surface of the header and the first major surface of test fanout layer, and disposing solder between a conductive pad disposed on the inner surface of the header and the patterned conductive layer.

Clause 79: The method of any one of clauses 71-78, where electrically connecting the header to the test fanout layer includes disposing an anisotropic conductive adhesive layer between the inner surface of the header and the test fanout layer.

Clause 80: The method of clause 79, where electrically connecting the header to the test fanout layer further includes disposing solder between the feedthrough pin and the patterned conductive layer The details of one or more aspects of the disclosure are set forth in the accompanying drawings and the description below. Other features, objects, and advantages of the techniques described in this disclosure will be apparent from the description and drawings, and from the claims.

8

Figure 1:
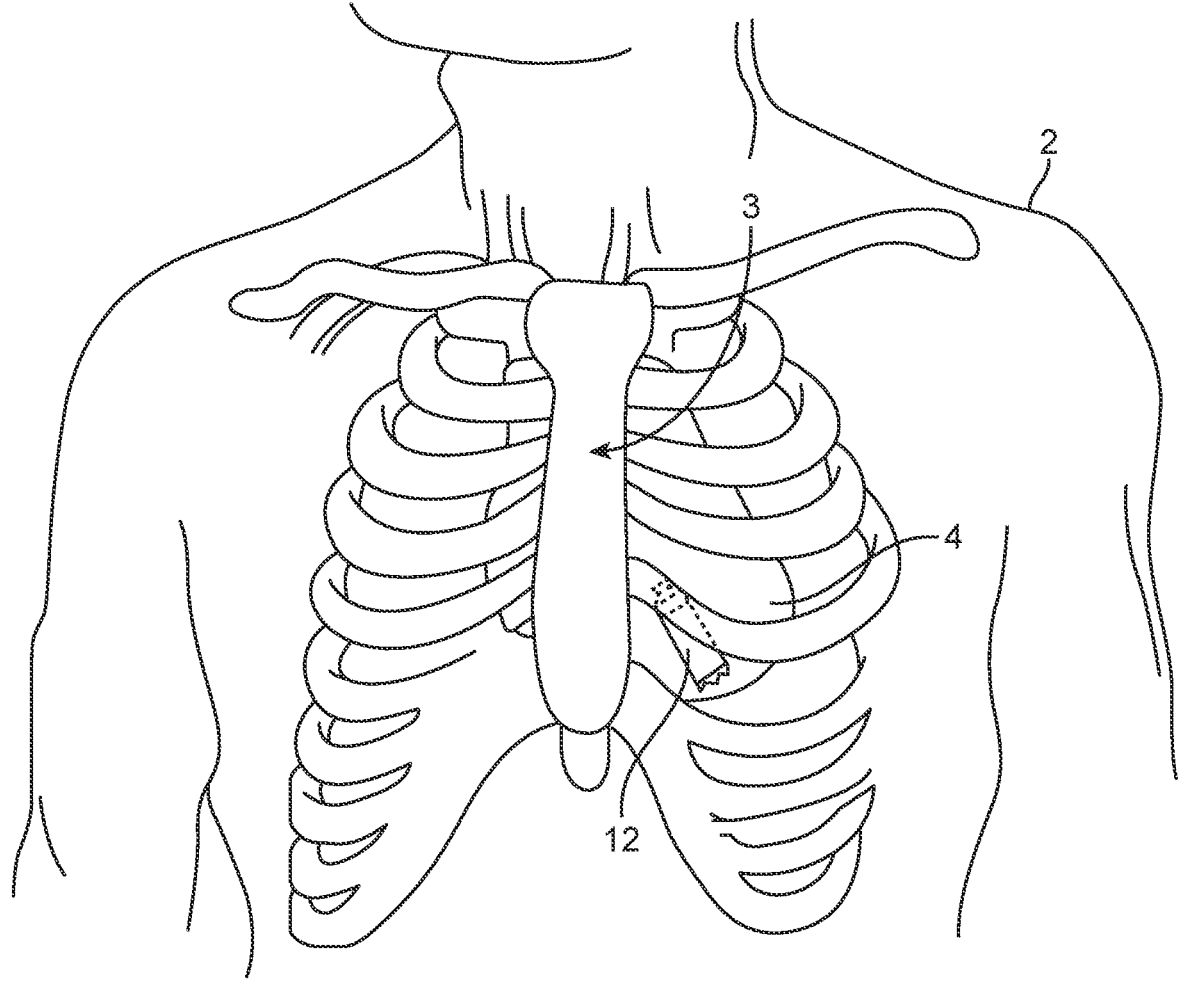
FIG. 1 is a schematic diagram of an implantable medical device disposed within a body of a patient.
Figure 2:
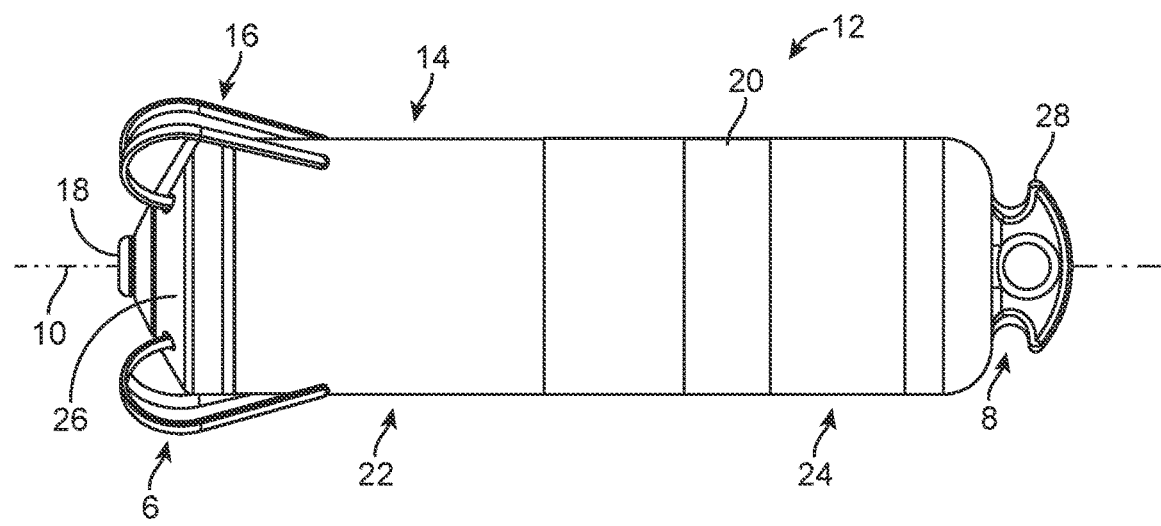

FIG. 2 is a schematic side view of the implantable medical device of FIG. 1.

Figure 3:
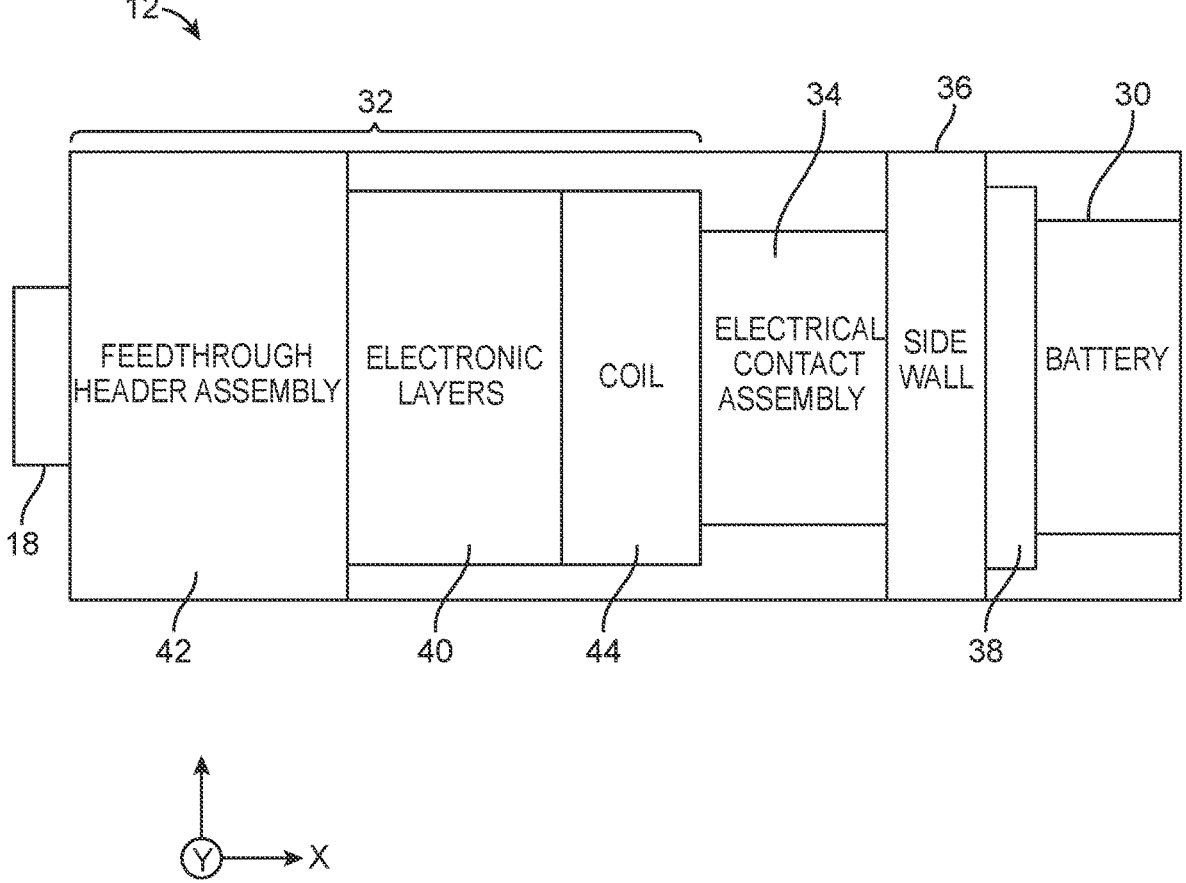

FIG. 3 is a schematic block diagram of the implantable medical device of FIG. 1.

Figure 4:
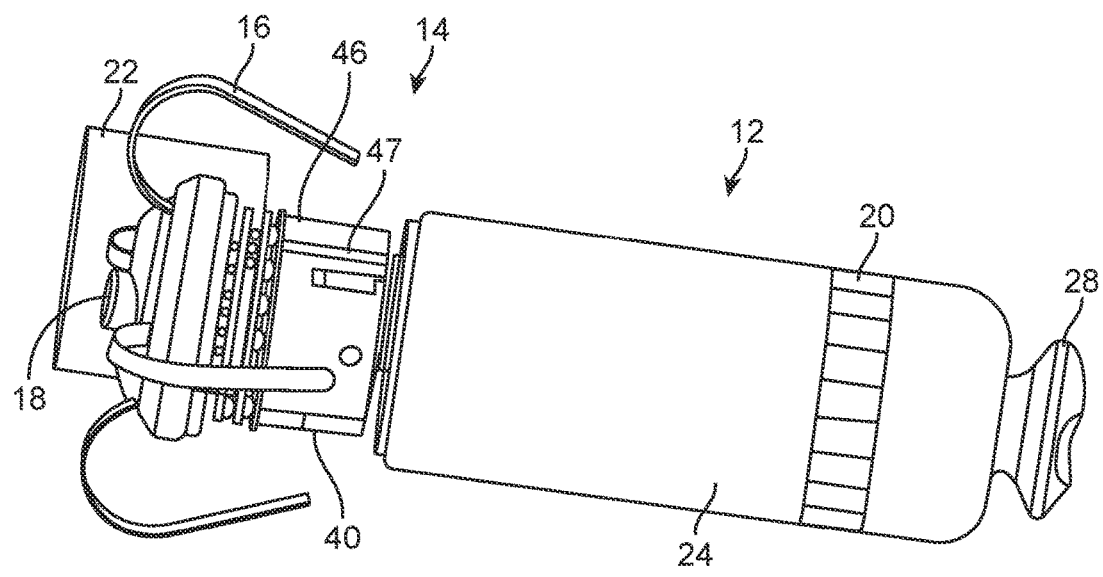

FIG. 4 is a schematic perspective view of the implantable medical device of FIG. 1 with a portion of the housing removed for clarity.

Figure 5:
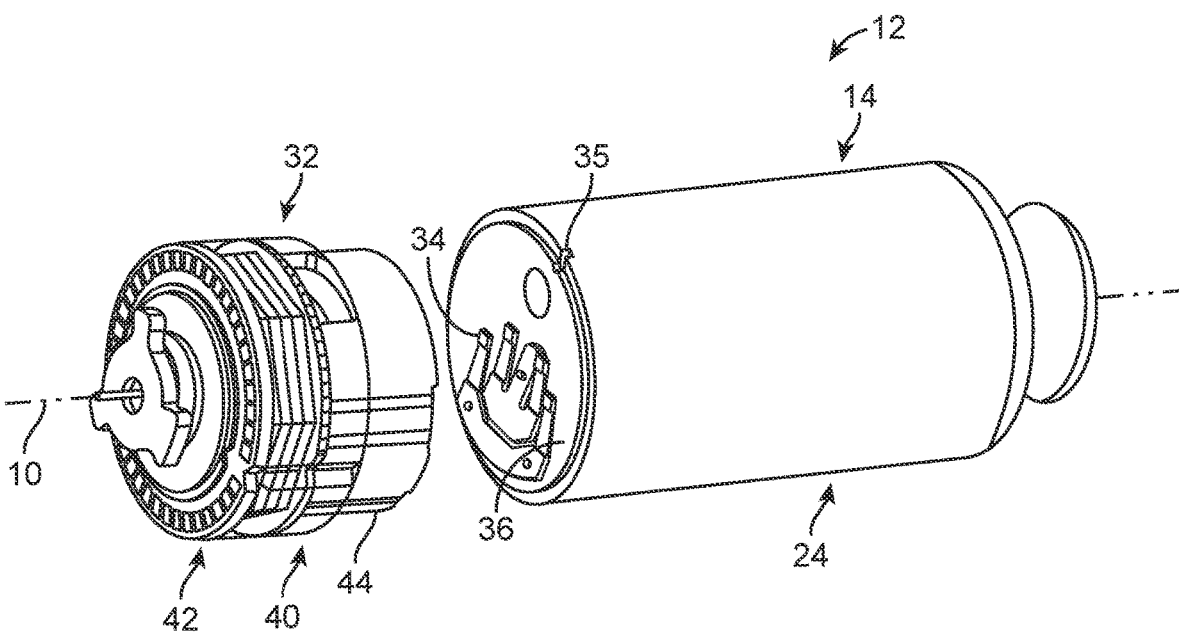

FIG. 5 is a schematic partially exploded view of the implantable medical device of FIG. 1 with a portion of the housing removed for clarity.

Figure 6:
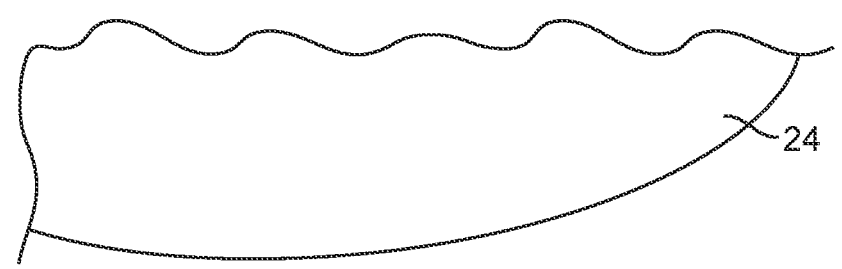

FIG. 6 is a schematic exploded view of an electronics module of the implantable medical device of FIG. 1.

Figure 7:
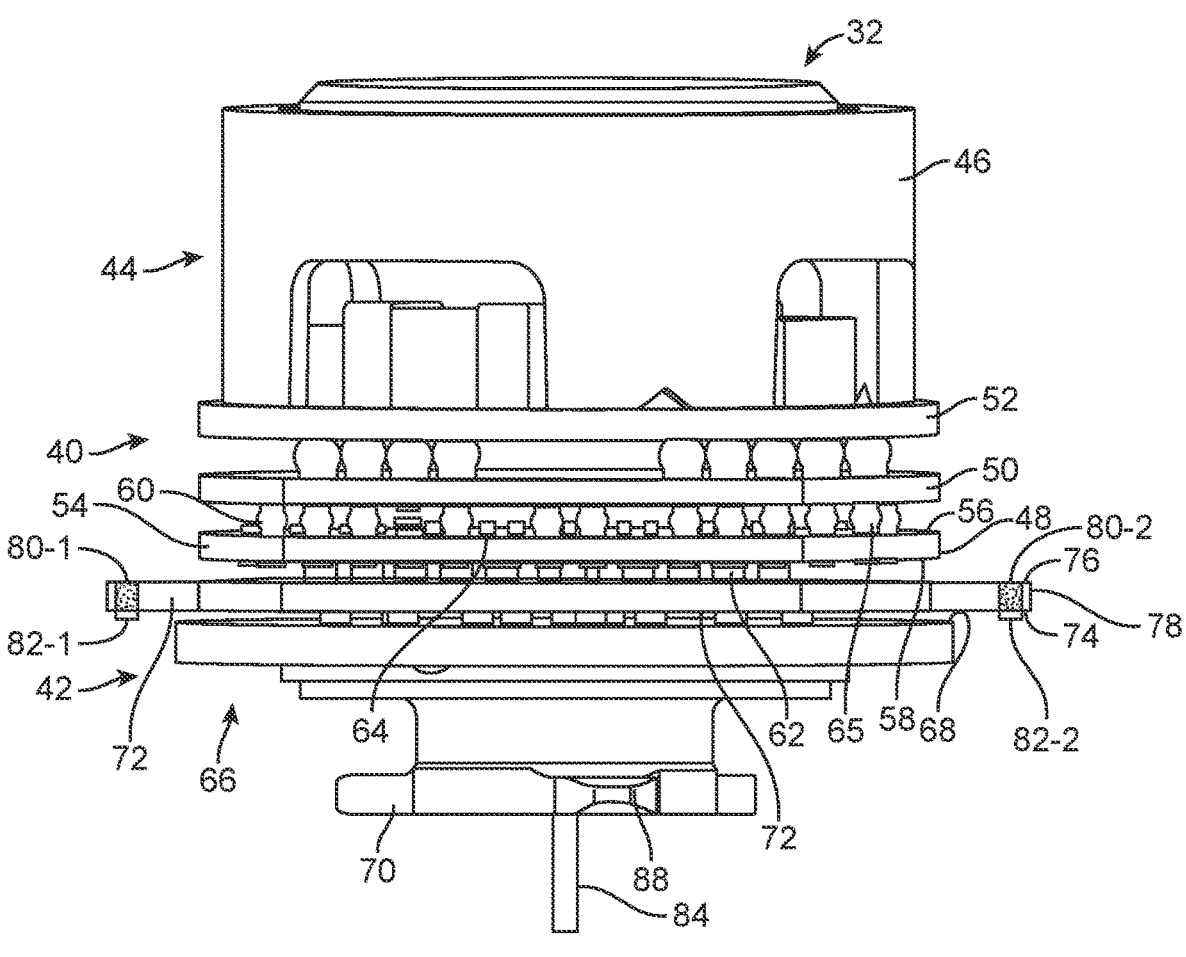

FIG. 7 is a schematic side view of the electronics module of the implantable medical device of FIG. 1.

Figure 8:
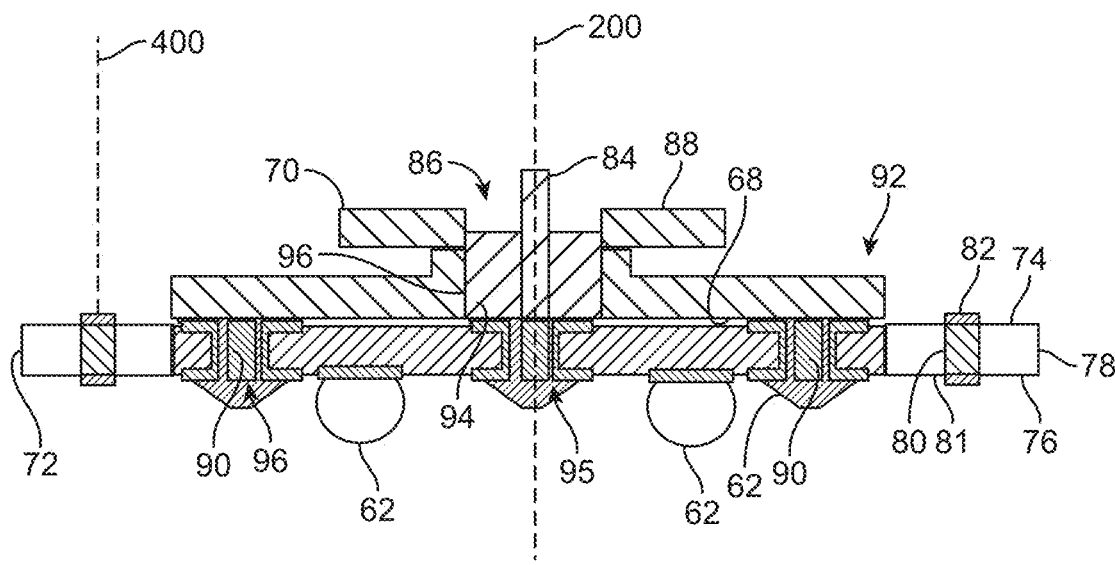

FIG. 8 is a schematic cross-section view of a feedthrough assembly of the implantable medical device of FIG. 1.

Figure 9:
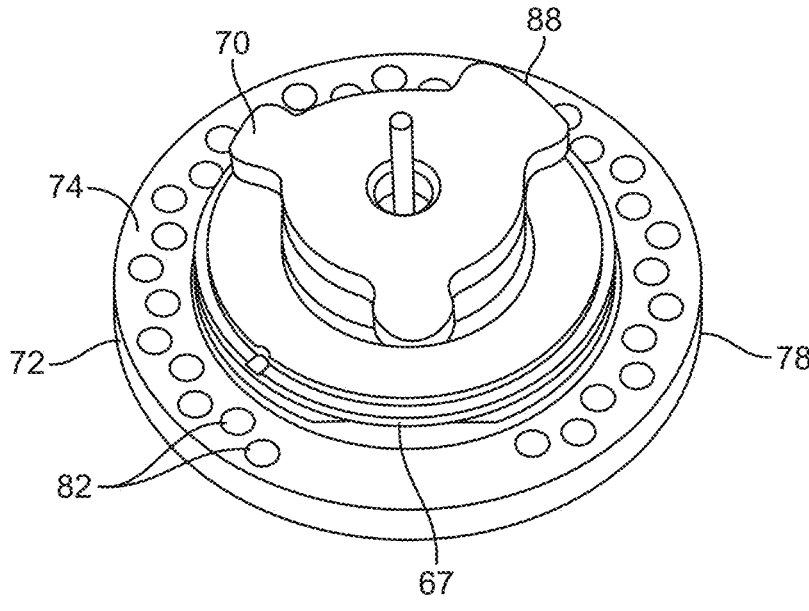

FIG. 9 is a schematic perspective view of the feedthrough assembly of FIG. 8.

Figure 10:
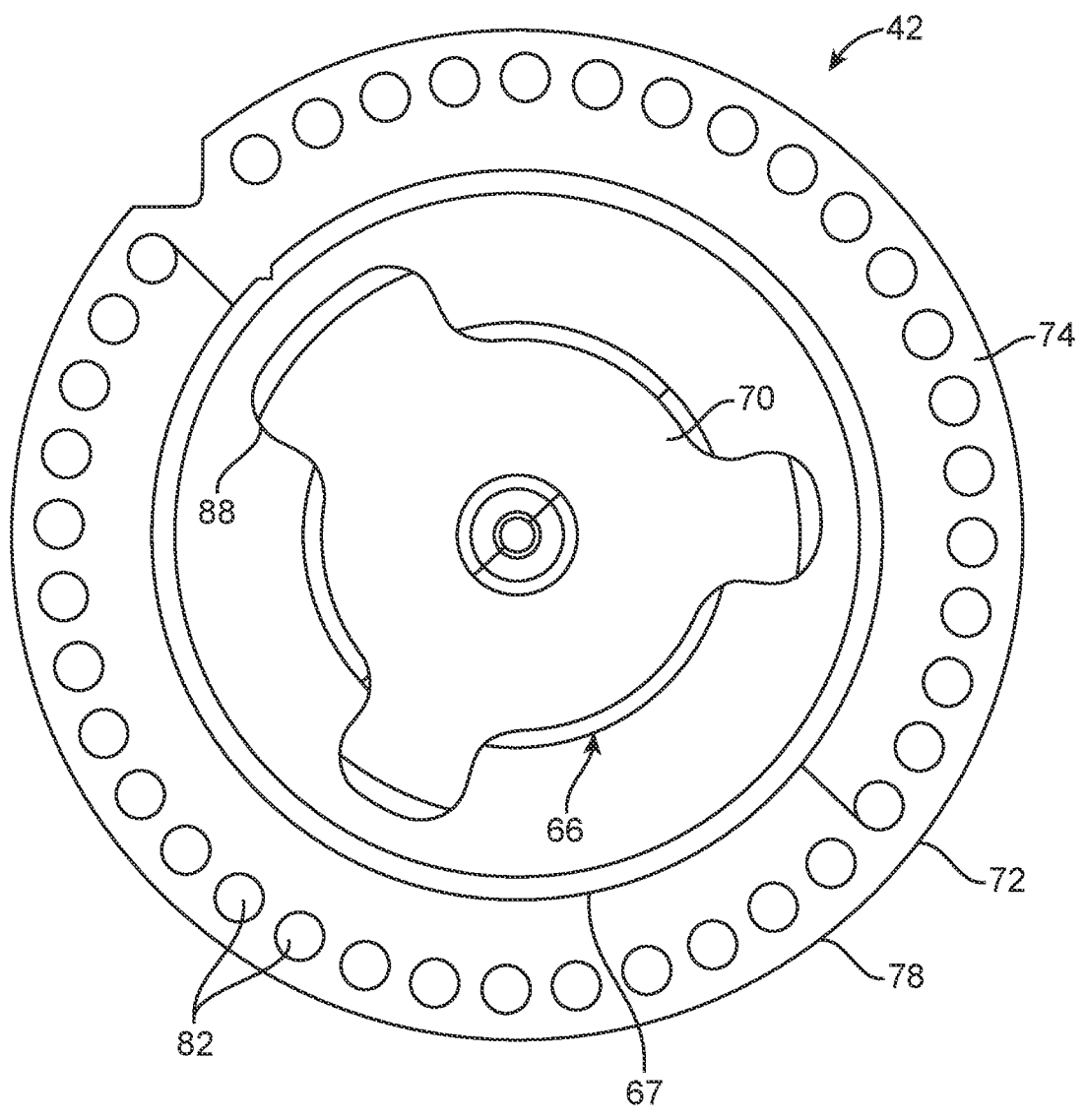

FIG. 10 is a schematic plan view of the feedthrough header assembly of FIG. 8.

Figure 11:
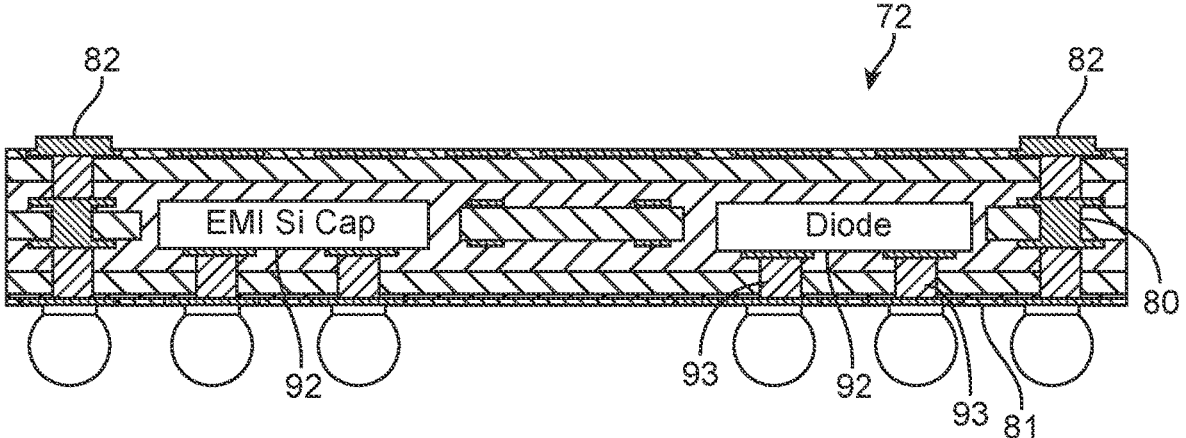

FIG. 11 is a schematic cross-section view of a test fanout layer of the feedthrough assembly of FIG. 8.

Figure 12:
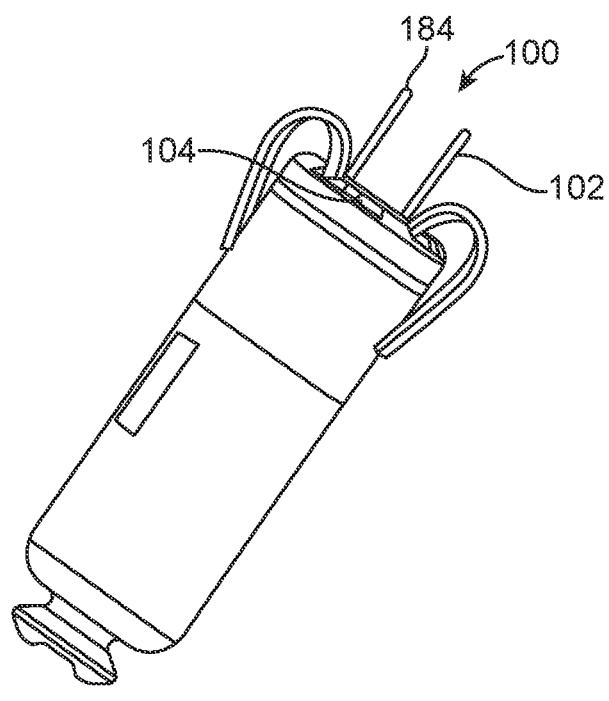

FIG. 12 is a schematic perspective view of another embodiment of an implantable medical device.

Figure 13:
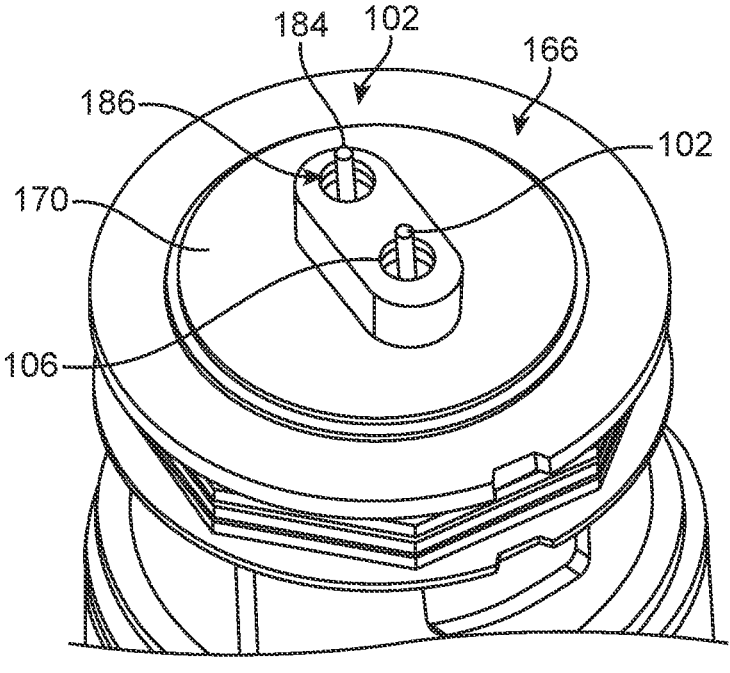

FIG. 13 is a schematic perspective view of the implantable medical device of FIG. 12 with an end cap of the device removed for clarity.

Figure 14:
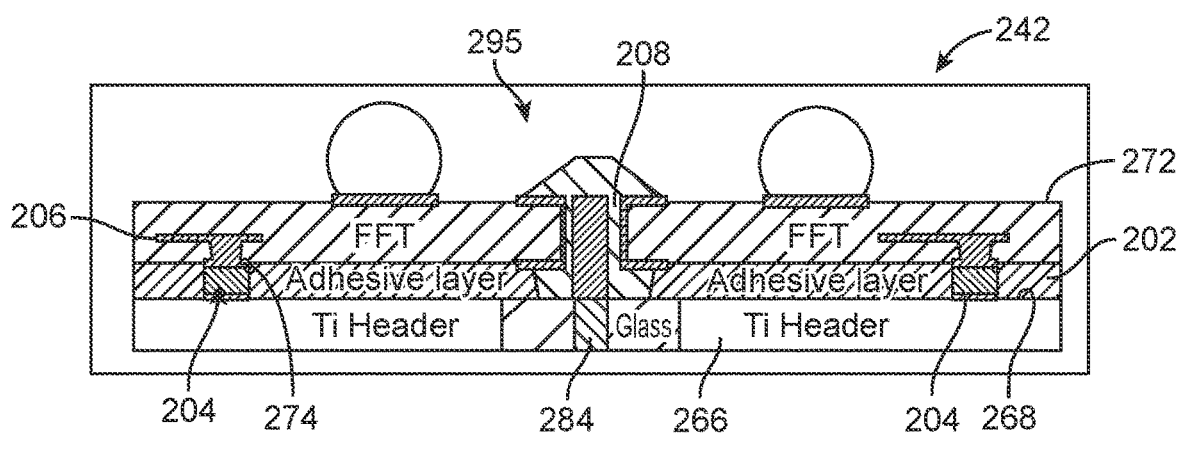

FIG. 14 is a schematic cross-section view of another embodiment of a feedthrough assembly.

Figure 15:
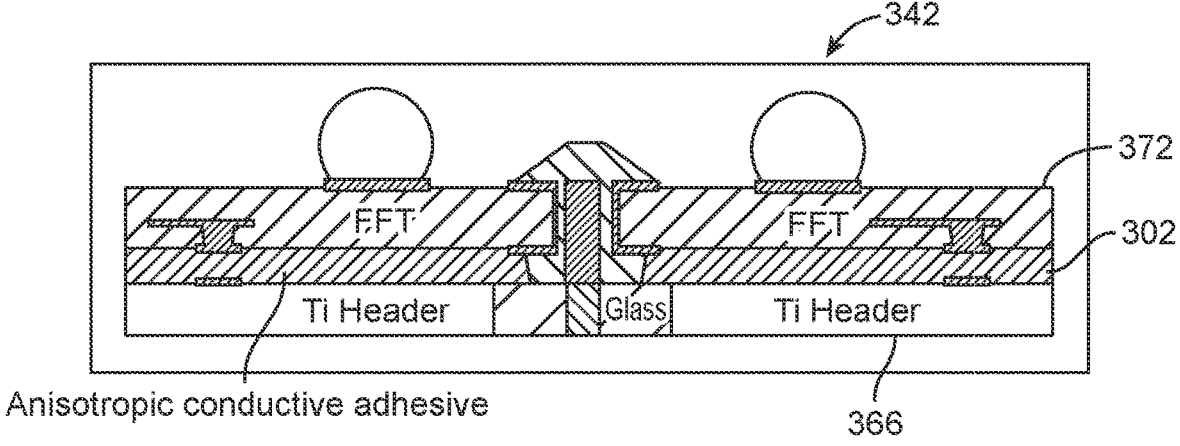

FIG. 15 is a schematic cross-section view of another embodiment of a feedthrough assembly.

Figure 16:
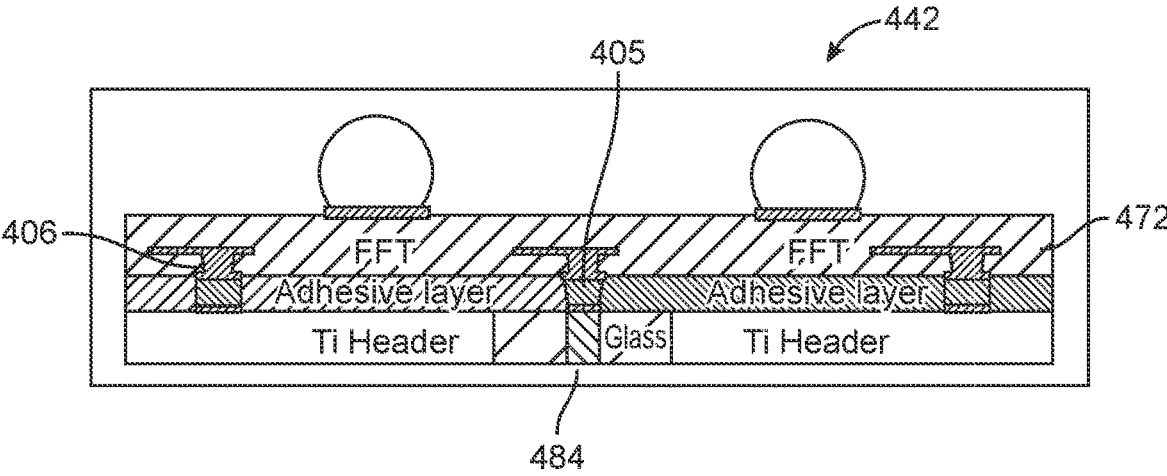

FIG. 16 is a schematic cross-section view of another embodiment of a feedthrough assembly.

Figure 17:
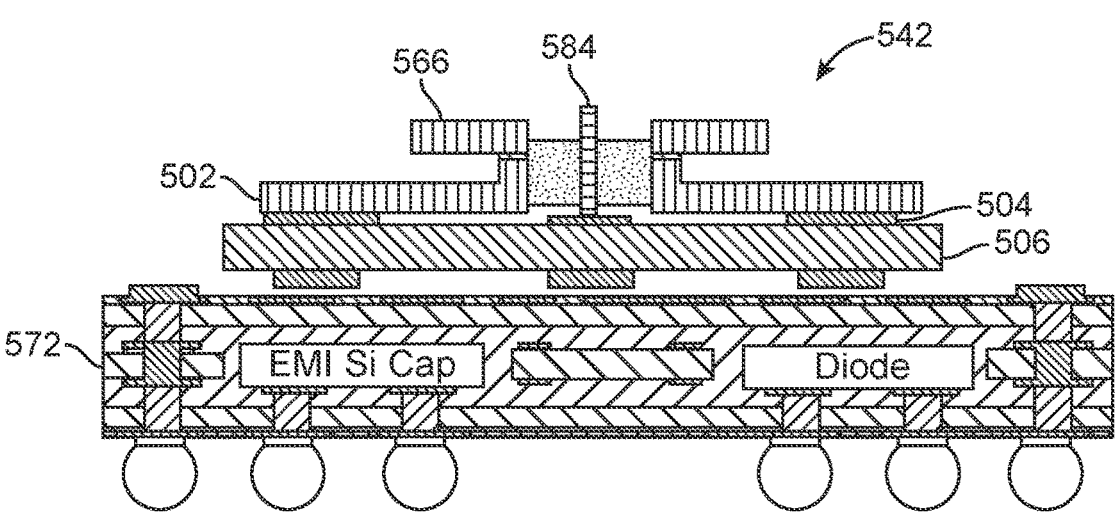

FIG. 17 is a schematic cross-section view of another embodiment of a feedthrough assembly.

Figure 18:
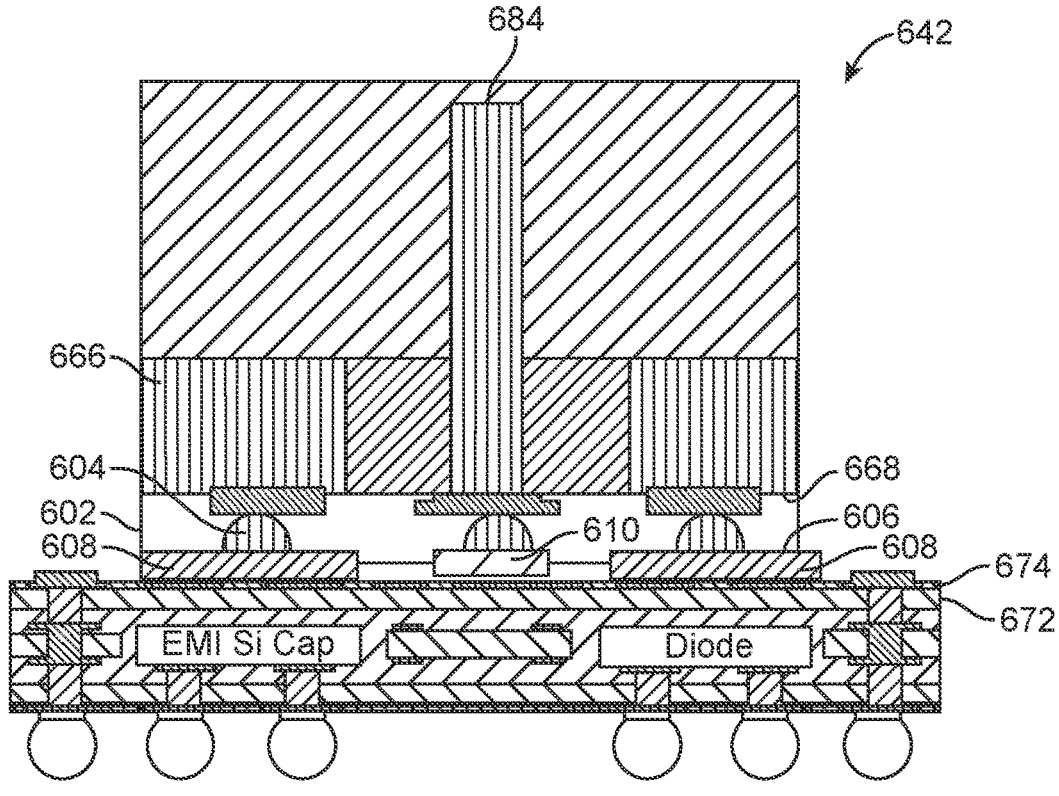

FIG. 18 is a schematic cross-section view of another embodiment of a feedthrough assembly.

FIG. 19 is a flowchart of one method of forming a feedthrough assembly.

DETAILED DESCRIPTION

The techniques of this disclosure generally relate to feedthrough assembly that includes a test fanout layer electrically connected to a header. The test fanout layer can include one or more test pads that are disposed on a first major surface of the test fanout layer that faces an inner surface of the header. At least one of the test pads can be electrically connected to an electronic component disposed on or in an electronic layer disposed facing a second major surface of the test fanout layer. The test pad can be adapted to allow for testing of the electronic component after the header, test fanout layer, and electronic layer have been connected.

The test pads can allow for testing during manufacture of one or more electronic components disposed on one or more electronic layers that are connected to the feedthrough assembly prior to such assembly being disposed within a housing, e.g., of an implantable medical device. Further, one or more embodiments of the present disclosure can include one or more electronic components disposed on or within the test fanout layer. Such components can include, e.g., a filter or filters that can be utilized to filter electrical signals that are transmitted to and received from at least one of the header or feedthrough pin of the assembly.

FIG. 1 is a schematic view of one embodiment of an implantable medical device 12 (IMD) disposed within a body of a patient 2. The IMD 12 can include any suitable medical device, e.g., a pacing device, pressure sensing device, cardiac monitor, other physiologic sensor, etc. The IMD 12 can include an arrangement of an electronics module and a feedthrough assembly as is further described herein. ID 12 can be, for example, an implantable leadless pacing device that is configured for implantation entirely within one of the chambers of a heart 4 and that provides electrical signals to the heart beneath a sternum 3 via electrodes carried on the housing of the device.

IMD 12 is generally described as being attached within a chamber of the heart 4 as an intracardiac pacing device. In one or more embodiments, IMD 12 can be attached to an external surface of the heart 4, such that the device is disposed outside of the heart but can pace a desired chamber. In one or more embodiments, IMD 12 is attached to an external surface of the heart 4 and one or more components of the device can be in contact with an epicardium of the heart. The IMD 12 is schematically shown in FIG. 1 attached to a wall of a ventricle of the heart 4 via one or more fixation components (e.g., tines, helix, etc.) that penetrate the tissue. These fixation components can secure the IMD 12 to the cardiac tissue and retain an electrode (e.g., a cathode or an anode) in contact with the cardiac tissue. IMD 12 can be implanted at or proximate to the apex of the heart. In one or more embodiments, a pacing device may be implanted at other ventricular locations, e.g., on the free-wall or septum, an atrial location, or any location on or within the heart 4.

FIG. 2 is a schematic side view of the IMD 12 of FIG. 1. In one or more embodiments, the IMD 12 is adapted to be implanted within a chamber of the heart 4 of the patient 2, e.g., to monitor electrical activity of the heart and/or provide electrical therapy to the heart. In the example shown in FIG. 2, the IMD 12 includes a housing 14, fixation components 16, and electrodes 18 and 20.

The housing 14 of the IMD 12 can include any suitable dimensions and take any suitable shape or shapes. The housing 14 extends between a first end 6 and a second end 8 along a longitudinal axis 10. In one or more embodiments, the housing 14 can have a cylindrical (e.g., pill-shaped) form factor. In one or more embodiments, the housing 14 includes an elongated tubular housing. Further, the housing 14 can include any suitable material or materials.

The IMD 12 can include fixation components adapted to fix pacing device 12 to tissue within the body of the patient 2. For example, in the embodiment illustrated in FIG. 2, the IMD 12 includes fixation tines 16 extending from the housing 14 that are adapted to engage with tissue to substantially fix a position of the housing within the patient 2. In one or more embodiments, the fixation tines 16 are adapted to anchor housing 14 to the cardiac tissue such that pacing device 12 moves along with the cardiac tissue during cardiac contractions. Fixation tines 16 can include any suitable material or materials, e.g., a shape memory material (e.g., Nitinol). Although the ID 12 includes a plurality of fixation tines 16 that are adapted to anchor the device to tissue, in one or more embodiments, the device can be fixed to tissue using other types of fixation mechanisms, such as, but not limited to, barbs, coils, helixes, and the like.

Housing 14, also referred to as an elongated housing, houses electronic components of the IMD 12, e.g., sensing circuitry for sensing electrical activity via electrodes 18 and 20 and therapy generation circuitry for delivering electrical stimulation therapy via the electrodes. Electronic components can include any discrete and/or integrated electronic circuit components that implement analog and/or digital circuits capable of producing the functions attributed to the IMD 12 described herein. In one or more embodiments, housing 14 can also house components for sensing other physiological parameters, such as acceleration, pressure, sound, and/or impedance. Although shown with two electrodes 18 and 20, the device 12 can include any suitable number of electrodes disposed in any suitable portion or portions of the housing.

Additionally, the housing 14 can also house a memory that includes instructions that, when executed by processing circuitry housed within housing, cause the IMD 12 to perform various functions attributed to the device herein. In one or more embodiments, the housing 14 can house communication circuitry that enables the IMD 12 to communicate with other electronic devices, such as a medical device programmer. In one or more embodiments, the housing 14 can house an antenna for wireless communication. The housing 14 can also house a power source, such as a battery. The housing 14 can be hermetically or near-hermetically sealed using any suitable technique or techniques to help prevent fluid ingress into the housing. For example, in one or more embodiments, one or more portions of the housing 14 can be hermetically sealed together utilizing one or more laser diffusion bonding techniques described in co-owned U.S. Pat. No. 10,124,559 B2, entitled KINETICALLY LIMITED NANO-SCALE DIFFUSION BOND STRUCTURES AND METHODS.

The IMD 12 includes the electrodes 18, 20 that can be connected to the housing utilizing any suitable technique or techniques. In one or more embodiment, at least one of the electrodes 18, 20 can be mechanically connected to the housing 14. In one or more embodiments, at least one of the electrodes 18, 20 can be defined by an outer portion of the housing 14 that is electrically conductive. For example, electrode 20 can be defined by a tissue-exposed conductive portion of the housing 14.

Electrodes 18, 20 are electrically isolated from each other. Electrode 18 can be referred to as a tip electrode, and fixation tines 16 can be adapted to anchor the IMD 12 to tissue such that electrode 18 maintains contact with the tissue. In one or more embodiments, fixation tines 16 can also be electrically connected to one or more electronic components such that the tines are adapted to direct an electrical signal to tissue of the patient and/or receive an electronic signal from the tissue. In one or more embodiments, a portion of the housing 14 can be covered by, or formed from, an insulative material to isolate electrodes 18 and 20 from each other and/or to provide a desired size and shape for one or both of electrodes.

Electrode 20 can be a portion of the housing 14, e.g., second portion 24, that does not include such insulative material. Electrode 20 can be most or all of housing 14, but most of the housing (other than electrode 20) can be covered with an insulative coating. In one or more embodiments, electrode 20 may be coated with materials to promote conduction. In one or more embodiments, electrode 20 can be part of a separate ring portion of housing 14 that is conductive. Electrodes 18, 20, which may include conductive portion(s) of the first portion 22 of housing 14, can be electrically connected to at least some electronics of pacing device 12 (e.g., sensing circuitry, electrical stimulation circuitry, or both). In one or more embodiments, the housing 14 can include an end cap 26, which can house or enclose a feedthrough assembly (e.g., feedthrough assembly 42 of FIG. 3) to electrically connect the electrode 18 to the electronics within the housing 14, while electrically isolating the electrode from the housing 14, e.g., including electrode 20 or other conductive portions of the housing.

In the embodiment illustrated in FIG. 2, the housing 14 includes a first portion 22 and a second portion 24. The first portion 22 can be disposed adjacent to the first end 6 of the housing 14, and the second portion 24 can be disposed adjacent to the second end 8 of the housing. As used herein, the term "adjacent to the first end" means that an element or component is disposed closer to the first end 6 of the housing 14 than to the second end 8 of the housing. Further, the term "adjacent to the second end" means that an element or component is disposed closer to the second end 8 of the housing 14 than to the first end 6 of the housing. The second portion 24 can, in one or more embodiments, define at least part of a power source case that houses a power source (e.g., a battery) of the IMD 12. In one or more embodiments, the second portion 24 can include the conductive portion of the housing 14 that forms the electrode 20.

The first portion 22 of the housing 14 can be connected to the second portion 24 of the housing using any suitable technique or techniques. In one or more embodiments, the first portion 22 of the housing 14 can be connected to the second portion 24 of the housing using laser bonding. For example, electromagnetic radiation (e.g., light) can be directed through an outer surface of the first portion 22 and focused at an interface between the first portion and the second portion 24 to form a laser bond.

In the embodiment of FIG. 2, the IMD 12 can also include a flange 28 connected to the second portion 24 of the housing 14 and at the second end 8 of the housing that defines an opening. The flange 28 can enable medical instruments to attach to the IMD 12, e.g., for delivery and/or extraction of the device. For example, a tether that extends through a catheter inserted into the heart 4 (FIG. 1) can be attached to the flange 28 and/or threaded through an opening of the flange to implant or extract the IMD 12.

FIG. 3 is a schematic block diagram of one embodiment of the IMD 12 including a power source 30 (e.g., battery), an electronics module 32, and an electrical contact assembly 34. Although the IMD of FIG. 3 is described as IMD 12, the structures shown in FIG. 3 can also be used in other implantable or external medical devices, such as cardioverter-defibrillators, physiological monitors, or neurostimulators, or any other electronic devices.

The housing 14 includes the first and second portions 22, 24 and a side wall 36 disposed within the housing between the battery 30 and the electrical contact assembly 34. The side wall 36 can be disposed within the first and second housing portions 22, 24 or at the boundary of first and second housing portions. In one or more embodiments, the first and second housing portions 22, 24 are common with a ground terminal of the battery 30. In one or more embodiments, at least one of the first or second housing portions 22, 24 is non-conductive. For example, first housing portion 22 can be formed of a non-conductive material, such as sapphire, which may allow easier transmission of electromagnetic signals into and out of the housing 14 than a metal or other conductive material would allow.

As shown in the embodiment illustrated in FIG. 3, the side wall 36 extends across housing 14 between the battery 30 on one side and the electrical contact assembly 34 on the other side. The side wall 36 can include at least one feedthrough (not shown) to allow for electrical connection between the battery 30 and the electronics module 32. As discussed herein, feedthrough assembly 42 can also include at least one feedthrough to allow for an electrical connection between electrode 18 and electronic layers 40. Electronics module 32 is disposed between the electrode 18 and electrical contact assembly 34. In one or more embodiments, electrical contact assembly 34 can be fixed to side wall 36 to provide mechanical support for the electronics module 32. The electronic contact assembly 34 provides an electrical connection between the battery 30 and the electronics module 32. For example, the electronics module 32 can include one or more electrical contacts that are adapted to electrically connect the module to the electronic contact assembly 34.

The IMD 12 can also include a battery header 38 disposed between the battery 30 and the electrical contact assembly 34. The side wall 36 can form part or all of the battery header 38. The battery header 38, the side wall 36, and the electrical contact assembly 34 can be electrically connected to the electronics module 32 using any suitable technique. In one or more embodiments, the battery header 38, the side wall 36, and/or electrical contact assembly 34 can include feedthroughs and/or openings for creating an electrical connection between the battery 30 and electronics module 32.

The electrical contact assembly 34 can include any suitable assembly for electrically connecting the electronics module 32 and the battery 30, e.g., one or more embodiments of electrical contact assemblies described in co-owned U.S. patent application Ser. No. 17/071,463, entitled ELECTRONICS ASSEMBLY FOR IMPLANTABLE MEDICAL DEVICE. In one or more embodiments, the electrical contact assembly 34 can include a spring contact for holding electronics module 32 in place and for providing electrical connections between the electronics module and the battery 30.

The IMD 12 can be manufactured utilizing a single tube for the first housing portion 22 or as two tube sections for such housing portion. Using a single tube for the housing portion 22, in contrast to two sections, e.g., two half-pipes, may lower the cost and complexity of the encasement for pacing device 12. A single tube opens up new encasement options and can be manufactured from alternate materials. For example, a single sapphire tube utilized for the first housing portion 22 can allow for wireless charging of the battery 30 even when the IMD 12 is implanted within a patient.

In one or more embodiments, at least one of the first and second portions 22, 24 of the housing 14 can include a substantially transparent material. As used herein, the phrase "substantially transparent" means that the material transmits greater than 50% of electromagnetic radiation incident on the material for a selected wavelength or range of wavelengths, assuming no reflection at the air-material boundaries. In one or more embodiments, at least one of the first and second portions 22, 24 can be substantially transmissive to electromagnetic radiation having a wavelength of at least 200 nm. In one or more embodiments, at least one of the first and second portions 22, 24 can be substantially transmissive to electromagnetic radiation having a wavelength of greater than 10,000 nm. In one or more embodiments, at least one of the first and second portions 22, 24 can be substantially transmissive to electromagnetic radiation having a wavelength in a range of 200 nm to 10,000 nm. In one or more embodiments, at least one of the first and second portions 22, 24 can be substantially transmissive to at least one of UV light, visible light, or IR light. The substantially transparent material can include at least one of glass, quartz, silica, sapphire, silicon carbide, diamond, or gallium nitride.

In one or more embodiments, the first housing portion 22 can include a substantially transparent material such that one or more sensors, emitters, or detectors can be disposed within the first housing portion and transmit or receive electromagnetic radiation through such portion. For example, FIG. 4 is a perspective view of the IMD 12 of FIGS. 1-3 with a transparent first portion 22 partially removed for clarity. As shown in FIG. 4, the electronics module 32 is disposed within the first portion 22.

The electronics module 32 can include any suitable elements or components. For example, as shown in FIG. 3, the electronics module 32 includes one or more electronic layers 40 and a feedthrough assembly 42 electrically connected to the one or more electronic layers 40. The electronics module 32 can also include one or more coils 44 electrically connected to the electronic layers 40.

FIGS. 5-7 are various views of the electronics module 32 of the pacing device 12 of FIGS. 1-4. The module 32 includes the electronic layers 40 and the feedthrough assembly 42 electrically connected to the electronic layers.

The electronic layers 40 include a first electronic layer 48, a second electronic layer 50, and a third electronic layer 52. Although illustrated as including three electronic layers, the electronic layers 40 can include any suitable number of layers, e.g., one, two, three, four, five, or more layers. Each layer of the electronic layers 40 can include a substrate. For example, first electronic layer 48 includes a substrate 54 having a first major surface 56 and a second major surface 58.

The electronic layers 40 can be disposed in any suitable relationship relative to the feedthrough assembly 42 and the battery 30. In one or more embodiments, the electronic layers 40 can be disposed such that they are substantially orthogonal to the longitudinal axis 10 (FIG. 5) of the IMD 12, where the housing 14 of the device extends along the longitudinal axis. For example, the first major surface 56 of the substrate 54 of the first electronic layer 48 is substantially orthogonal to the longitudinal axis 10 of the housing 14. As used herein, the term "substantially orthogonal" means that the longitudinal axis 10 forms an angle with a substrate of one or more of the electronic layers 40 of no greater than 10 degrees.

The electronic layers 40 can be electrically connected together using any suitable technique. In or more embodiments, one or more of the electronic layers 40 can include one or more conductive vias that are disposed through the respective substrate of one or more of the electronic layers. Further, one or more conductive pads 60 can be disposed on one or more of the conductive layers 40 to provide electrical connections between the feedthrough assembly 42 and the conductive layers, between one or more of the conductive layers, and between the conductive layers and the electrical contact assembly 34. For example, conductive pad 62 is disposed between (e.g., between conductive surfaces of) the feedthrough assembly 42 and the first electronic layer 48 to provide an electrical connection between the feedthrough assembly and the first electronic layer. In one or more embodiments, this connection can be between the housing 14 and the first electronic layer 48 or between one or more feedthrough pins 84 of the assembly and the first electronic layer. The conductive pads 60 can include any suitable conductive contact, e.g., solder bumps, solder balls, conductive epoxy, braze alloys, etc.

One or more of the electronic layers 40 can include an electronic component disposed on its respective substrate. For example, first electronic layer 48 includes electronic component 64 disposed on the first major surface 56 of the substrate 54. The electronic component 64 can be disposed on at least one of the first major surface 56 or second major surface 58 of the substrate 54. Any suitable number of electronic components can be disposed on one or both major surfaces 56, 58 of the substrate 54. Further, the electronic component 64 can be electrically connected to one or more additional electronic components disposed on the substrate 54 or on the second or third electronic layers 50, 52 using any suitable technique or techniques. In one or more embodiments, the electronic component 64 can be disposed on a patterned conductive layer (not shown) disposed on the substrate 54 using any suitable technique or techniques. One or more conductive vias can be disposed between the first and second major surfaces 56, 58 of the substrate 54 to provide one or more conductive pathways between the patterned conductive layer and other elements or components disposed on an opposite side of the substrate 54 from the electronic component. Further, one or more conductive pads 60 can be directly connected to the electronic component 64 to electrically connect the component to one or more additional components or devices.

Electrically connected to one or more of the electronic layers 40 is the coil 44. Such coil 44 can include any suitable number of coils disposed on or within a housing 46 and one or more electronic components also disposed within the housing. The coil 44 can be utilized to inductively couple the IMD 12 with an external inductive charging system for charging the device when it is implanted within the body of the patient 4 or for telemetry or other types of communication with a transceiver that is external to the patient's body. The coil 44 can be electrically connected to the electronic layers 40 using any suitable technique. Further, the coil 44 can be electrically connected, e.g., to electronic layer 52 using any suitable technique. The housing 46 of the coil 44 can provide one or more electrical pathways between the battery 30 and the electronic layers 40 using any suitable technique. In one or more embodiments, one or more conductors 47 (FIG. 4) can be disposed on or within housing 46 to provide one or more of these electrical pathways.

Also electrically connected to one or more of the electronic layers 40 is the feedthrough assembly 42. As shown in FIGS. 6-11, the assembly 42 includes a header 66 that has an inner surface 68 and an outer surface 70. The assembly 42 further includes a test fanout layer 72 that has a first major surface 74 and a second major surface 76. The test fanout layer 72 also includes a perimeter 78. The first major surface 74 of the test fanout layer 72 faces the inner surface 68 of the header 66. In one or more embodiments, the first major surface 74 of the test fanout layer 72 is disposed adjacent to the inner surface 68 of the header 66. As used herein, the term "adjacent to the inner surface" means that an element or component is disposed closer to the inner surface 68 of the header than to the outer surface 70 of the header.

As shown in FIG. 8, the test fanout layer 72 also includes a test via 80 that extends between the first major surface 74 and the second major surface 76 of the test fanout layer, and a test pad 82 disposed on the first major surface of the test fanout layer and electrically connected to the test via. At least a portion of the test pad 82 is disposed between the outer surface 70 of the header and the perimeter 78 of the test fanout layer 72 as viewed in a plane parallel to the first major surface 74 of the test fanout layer (i.e., the plane of FIG. 10) such that the at least a portion of the test pad is exposed. As used herein, the term "exposed" means that the test pad 82 is accessible for contacting with a test probe prior to the end cap 26 (FIG. 2) being disposed over the header 66 and connected to the housing 46 of the implantable medical device 12.

The assembly 42 can take any suitable shape or shapes and have any suitable dimensions. In one or more embodiments, the assembly 42 can include an elliptical cross-section in a plane substantially parallel to a first major surface 74 of the test fanout layer 72 (i.e., the plane of FIG. 10).

The header 66 can also take any suitable shape or shapes and have any suitable dimensions. Further, the header 66 can include any suitable material or materials, e.g., at least one of titanium, copper, niobium, tantalum, or alloys thereof. In one or more embodiments, the header 66 is electrically conductive.

The header 66 can include a flange 88 that at least in part forms the outer surface 70 of the header. The flange 88 can be adapted to connect the header 66 to the end cap 26 (FIG. 2). Further, the header 66 can include one or more conductive posts 90 (FIG. 8), where each conductive post extends from the inner surface 68. The conductive posts 90 can take any suitable shape or shapes and have any suitable dimensions. Further, the header 66 can include any suitable number of conductive posts 90, e.g., one, two, three, four, five, or more conductive projections. The conductive posts 90 can be formed integrally with the header 66. In one or more embodiments, the conductive posts 90 can be deposited onto or connected to the inner surface 68 of the header 66 using any suitable technique or techniques.

The conductive posts 90 are electrically connected to the header 66. In one or more embodiments, the test fanout layer 72 is electrically connected to the header 66 utilizing the conductive posts 90. One or more of the conductive posts 90 can be electrically connected to a metallized through hole 96 of the test fanout layer 72, where the metallized through hole extends between the first major surface 74 and the second major surface 76 of the test fanout layer. In one or more embodiments, one or more conductive posts 90 extend from the inner surface 68 of the header 66 through the test fanout layer 72 to the first electronic layer 48. Any suitable technique can be utilized to electrically connect the conductive posts 90 to the first electronic layer 48, e.g., soldering, welding, conductive epoxy, etc.

As is further described herein, the feedthrough pin 84 can be disposed within a first header via 86 that extends through the header 66. The feedthrough pin 84 extends outward beyond the outer surface 70 of the header 66 and can also extend through a metallized through hole 95 that extends between the first major surface 74 and the second major surface 76 of the test fanout layer 72 such that the feedthrough pin is electrically connected to the metallized through hole. In such embodiments, the metallized through hole 95 electrically connected to the feedthrough pin 84 can be considered a first metallized through hole, and the metallized through hole 96 electrically connected to the conductive post 90 can be considered the second metallized through hole 96.

Electrically connected to the header 66 is the test fanout layer 72. The test fanout layer 72 can take any suitable shape or shapes and have any suitable dimensions. In one or more embodiments, the test fanout layer 72 can take a substantially elliptical shape (e.g., circular shape) that can extend beyond an outer perimeter 67 of the header 66 as shown in FIG. 10. In one or more embodiments, the test fanout layer 72 can take a first shape (e.g., rectangular shape) during manufacturing, and one or more portions of the test fanout layer can be subsequently removed such that the test fanout layer takes an elliptical shape as shown in FIG. 10. In one or more embodiments, the test fanout layer 72 can include any suitable dielectric material or materials, e.g., at least one of polyimide, polyester, or mylar. Further, the test fanout layer 72 can include one or more layers of material that are connected together using any suitable technique or techniques.

The first major surface 74 of the test fanout layer 72 faces the inner surface 68 of the header 66. As used herein, the term "faces" does not require direct adjacency between two components, e.g., one or more additional components may be disposed between the first major surface 74 of the test fanout layer 72 and the inner surface 68 of the header 66. In one or more embodiments, the test fanout layer 72 can be disposed on an and in contact with the inner surface 68 of the header 66. Further, in one or more embodiments, one or more additional layers or components (e.g., an adhesive layer) can be disposed between the first major surface 74 of the test fanout layer 72 and the inner surface 68 of the header 66.

Disposed in the test fanout layer 72 is the one or more test vias 80. The test fanout layer 72 can include any suitable number of test vias 80. Further, the test vias 80 can be disposed in any suitable portion or portions of the test fanout layer 72. The test vias 80 can take any suitable shape or shapes and have any suitable dimensions. Each test via 80 include a conductive material or materials that are adapted to electrically connect the test pads 82 and one or more electronic components disposed on or within one or more of the electronic layers 40 or the test fanout layer 72 as is further described herein.

The test fanout layer 72 further includes one or more test pads 82 disposed on or in the first major surface 74 of the layer. A normal 400 to each of one or more test pads 82 is substantially parallel to a longitudinal axis 200 of the assembly 42 that is substantially orthogonal to the first and second major surfaces of the test fanout layer 72. Each test pad 82 can be electrically connected to a test via 80 using any suitable technique. The test fanout layer 72 can include any suitable number of test pads 82 disposed in any suitable portion or portions of the test fanout layer. In one or more embodiments, the assembly 42 can include a plurality of test pads 82 disposed on the test fanout layer 72, where each test pad of the plurality test pads is electrically connected to a test via 80 that extends between the first major surface 74 and the second major surface 76 of the test fanout layer. In one or more embodiments, the test pads 82 can be disposed in a pattern or array on or within the test fanout layer 72. For example, as shown in FIG. 10, the test pads 82 are disposed in a circular pattern on or within the test fanout layer 72.

Each test pad 82 can take any suitable shape or shapes and have any suitable dimensions. In one or more embodiments, a cross-sectional shape of one or more test pads 82 in a plane parallel to the first major surface 74 of the test fanout layer 72 can be the same as a cross-sectional shape in the same plane of the connected test via 82. Further, each test pad 82 can include any suitable conductive material or materials, e.g., the same materials utilized to form the test vias 80.

At least a portion of one or more of the test pads 82 can be disposed between the outer surface 70 of the header 66 and the perimeter 78 of the test fanout layer 72 as viewed in a plane parallel to the first major surface 74 of the test fanout layer (e.g., the plane of FIG. 10) such that the at least a portion of the test pad is exposed. In other words, such portion of the test pad 82 is accessible by a test probe prior to the end cap 26 of the IMD 12 being disposed over the header 66 of the feedthrough assembly. Such exposure of at least a portion of one or more of the test pads 82 allows testing of one or more electronic components disposed on or within one or more of the electronic layers 42 or the test fanout layer prior to completion of the assembly of the implantable medical device 12. As such, each test pad 82 can be electrically connected to one or more electronic components of the electronic layers 42 using any suitable techniques. For example, one or test pads 82 can be electrically connected to one or more electronic components utilizing one or more test vias 80. As shown in FIG. 7, test pad 82-1 is electrically connected to electronic component 64 of the first electronic layer 48, e.g., by a first test via 80-1. Further, the test fanout layer 72 can include a second test pad 82-2 that is electrically connected to a second electronic component 65 of the first electronic layer 48, e.g., by a second test via 80-2. Although the first and second test pads 82-1 and 82-2 are each electrically connected to first and second electronic components 64 and 65 of the first electronic layer 48, one or more of the test pads 82 can be electrically connected to electronic components disposed on at least one of the second electronic layer 50 or the third electronic layer 52.

Further, one or more conductors 81 can be disposed on the second major surface 76 of the test fanout layer 72 that electrically connects the test via 82 to one or more conductive pads 62 disposed on the second major surface of the test fanout layer. Such conductive pads 62 can be electrically connected to conductive pads of the electronic layers 42 that are in turn electrically connected to one or more electronic components of the electronic layers. As is further described herein, one or more test pads 82 can also be electrically connected to one or more electronic components disposed on or within the test fanout layer 72.

The feedthrough assembly 42 can also include the feedthrough pin 84 disposed within the header via 86 that extends through the header 66 as shown, e.g., in FIG. 8. The feedthrough pin 84 can extend outward beyond the outer surface 70 of the header 66 any suitable distance. In one or more embodiments, the feedthrough pin 84 also extends into the metallized through hole 95 that extends between the first major surface 74 and the second major surface 76 of the test fanout layer 72 such that the feedthrough pin is electrically connected to the metallized through hole, e.g., by a conductive material disposed between the feedthrough pin and the metallized through hole. In one or more embodiments, the feedthrough pin 84 extends through the metallized through hole 95 and beyond the second major surface 76 of the test fanout layer 72.

As shown in FIG. 8, insulating material 94 can be disposed between the feedthrough pin 84 and at least a portion 96 of the via 86 disposed through the header 66 such that the feedthrough pin is electrically isolated from the header. Any suitable insulating material 94 can be utilized to isolate the feedthrough pin 84 within the via 86, e.g., glass, sapphire, epoxy, or other non-conductive material that provides a seal, etc.

Although depicted as including one feedthrough pin 84, the feedthrough assembly 42 can include any suitable number of feedthrough pins, e.g., two, three, four, five, or more feedthrough pins. For example, FIGS. 12-13 are various views of another embodiment of an implantable medical device 100. All of the design considerations and possibilities of the pacing device 12 of FIGS. 1-10 apply equally to the implantable medical device 100 of FIGS. 12-13.

One difference between device 100 and device 12 is that device 100 includes a first feedthrough pin 184 and a second feedthrough pin 102 that extend from an endcap 104 of the device. Each of the feedthrough pins 102, 184 can be electrically connected to a test fanout layer (e.g., test fanout layer 72 of FIG. 8). Further, the first feedthrough pin 184 can be disposed within a first header via 186, and the second feedthrough pin 102 can be disposed in a second header via 106, where each of the header vias extends through a header 166. In one or more embodiments, two or more of the feedthrough pins 102, 184 can be disposed in the same via and electrically isolated using an insulating material. Further, each of the feedthrough pins 102, 184 can extend beyond an outer surface 170 of the header as shown in FIG. 13.

Returning to FIGS. 1-11, the feedthrough assembly 42 can further include one or more electronic components. For example, as shown in FIG. 11, which is a schematic cross-section view of the test fanout layer 72 of FIGS. 1-10, the layer 72 includes one or more electronic components 92 disposed within the layer in any suitable location. In one or more embodiments, one or more electronic components 92 can be disposed on at least one of the first major surface 74 or the second major surface 76 of the test fanout layer 72. At least one of the electronic components 92 can be electrically connected to the header 66. Further, in one or more embodiments, at least one of the electronic components 92 can be electrically connected to the feedthrough pin 84. Further, the electronic components 92 can be electrically connected to at least one of the header 66 or the feedthrough pin 84 utilizing any suitable technique. The electronic components 92 can include any suitable circuitry or components, e.g., at least one of a capacitor, diode, filter, etc.

The electronic components 92 can be electrically connected to one or more test pads 82 using any suitable technique. In one or more embodiments, one or more conductors 81 can be electrically connected to a test pad 82 by the test via 80 and also electrically connected to an electronic component 92 through one or more conductive vias 93 disposed between the electronic component and the conductor 81. The conductor 81 can be disposed on at least one of the first major surface 74 or second major surface 76, or within the test fanout layer 72. Further, in one or more embodiments, the header 66 can be electrically connected to one or more electronic components 92 of the test fanout layer 72 using any suitable technique. In one or more embodiments, the feedthrough pin 84 can be electrically connected to one or more electronic components 92 of the test fanout layer 72 using any suitable technique.

As mentioned herein, the header 66 can be electrically connected to the test fanout layer 72 using any suitable technique. For example, FIG. 14 is a schematic cross-section view of a portion of another embodiment of a feedthrough assembly 242. All of the design considerations and possibilities regarding the feedthrough assembly 42 of FIGS. 1-11 apply equally to the feedthrough assembly 242 of FIG. 14. Feedthrough assembly 242 includes an adhesive layer 202 disposed between an inner surface 268 of a header 266 and a test fanout layer 272. The adhesive layer 202 can include any suitable adhesive or adhesives. In one or more embodiments, the adhesive layer 202 mechanically connects the header 266 to the test fanout layer 272. Electrical connection can be provided by solder 204 or an electrically conductive adhesive disposed between the header 266 and a pattern conductive layer 206 disposed on a first major surface 274 of the test fanout layer 272. In such embodiments, the adhesive layer 202 can be a patterned adhesive layer that includes the solder 204 disposed therein. Such embedded conductive adhesive layer 202 can be disposed onto either the test fanout layer 272 or the header 266 using any suitable technique, and the header and test fanout layer can be positioned such that the adhesive layer is disposed between the header and the test fanout layer. The adhesive layer 202 can be cured before, after, or simultaneously with reflow of the solder 204.

Feedthrough assembly 242 can also include a feedthrough pin 284 that can be electrically connected to a metallized via 295 of the test fanout layer 272 using any suitable technique. In one or more embodiments, the feedthrough pin 284 can be electrically connected to the metallized via 295 by utilizing a solder joint 208 that is disposed between the feedthrough pin and the metallized via. Any suitable technique can be utilized to form the solder joint 208.

Further, in one or more embodiments, the adhesive layer 202 can electrically connect the header 266 to the test fanout layer 272. For example, FIG. 15 is a schematic cross-section view of another embodiment of a feedthrough assembly 342. All of the design considerations and possibilities regarding the feedthrough assembly 42 of FIGS. 1-11 and the feedthrough assembly 242 of FIG. 14 apply equally to the feedthrough assembly 342 of FIG. 15. One difference between feedthrough assembly 342 and feedthrough assembly 242 is that assembly 342 includes an adhesive layer 302 that includes an anisotropic conductive adhesive that is adapted to electrically connect header 366 to test fanout layer 372. Because the adhesive layer 302 is electrically conductive, solder or separate conductive adhesive is no longer required to electrically connect the header 366 to a patterned conductive layer 306 disposed on the test fanout layer 372.

A feedthrough pin of a feedthrough assembly can also be electrically connected to a patterned conductive layer of a test fanout layer using any suitable technique. For example, FIG. 16 is a schematic cross-section view of another embodiment of a feedthrough assembly 442. All of the design considerations and possibilities regarding the feedthrough assembly 42 of FIGS. 1-11 and the feedthrough assembly 242 of FIG. 14 apply equally to the feedthrough assembly for 42 of FIG. 16.

One difference between the feedthrough assembly 442 of FIG. 16 and feedthrough assembly 242 of FIG. 14 is that feedthrough pin 484 is electrically connected to a patterned conductive layer 406 disposed on a test fanout layer 472 by solder 405 disposed between the patterned conductive layer and the feedthrough pin. Any suitable technique can be utilized to dispose the solder 405 between the feedthrough pin 484 and the patterned conductive layer 406.

As mentioned herein, any suitable technique can be utilized to electrically connect a header to a test fanout layer of a feedthrough assembly. For example, FIG. 17 is a schematic cross-section view of another embodiment of a feedthrough assembly 542. All of the design considerations and possibilities regarding the feedthrough assembly 42 of FIGS. 1-11 apply equally to the feedthrough assembly 542 of FIG. 17. Feedthrough assembly 542 includes a redistribution layer 502 disposed between a header 566 and a test fanout layer 572. The header 566 and a feedthrough pin 584 of the assembly 542 are electrically connected to test fanout layer 572 utilizing the redistribution layer 502. The redistribution layer 502 can include any suitable material or materials, e.g., the same materials described herein regarding the test fanout layer 572. The redistribution layer 502 can include conductive vias 504 that are disposed through a substrate 506 of the redistribution layer. Such conductive vias 504 can electrically connect the header 566 and the feedthrough pin 584 to the test fanout layer 572. The header 566 and the feedthrough Penn 584 can be electrically connected to the redistribution layer 502 using any suitable technique. Similarly, the redistribution layer 502 can be electrically connected to the test fanout layer 572 using any suitable technique.

FIG. 18 is a schematic cross-section view of another embodiment of a feedthrough assembly 642. All of the design considerations and possibilities regarding the feedthrough assembly 42 of FIGS. 1-11 apply equally to the feedthrough assembly 642 of FIG. 18. As shown in FIG. 18, one or more conductive pads 602 can be disposed on an inner surface 668 of a header 666 and a feedthrough pin 684. Such conductive pads 604 can be adapted to electrically connect the header 666 and the feedthrough pin 684 to a test fanout layer 672 using any suitable technique. The conductive pads 604 can include any suitable conductive material and be disposed between the header 666 and feedthrough pin 684 and the test fanout layer 672 using any suitable technique. In one or more embodiments, an adhesive layer 602 can be disposed between the header 666 and the test fanout layer 672 that is adapted to mechanically connect the header to the test fanout layer.

In one or more embodiments, the header 666 is electrically connected to the test fanout layer 672 by a patterned conductive layer 606 disposed on a first major surface 674 of the test fanout layer 672. The patterned conductive layer 606 can be disposed in any suitable pattern or patterns on the first major surface 674 or within the layer 672. In one or more embodiments, the patterned conductive layer 606 includes a first conductive portion 608 and a second conductive portion 610 that is electrically isolated from the first conductive portion. The first conductive portion 608 can be electrically connected to the header 666 by one or more conductive pads or posts 604. Further, the feedthrough pin 684 can be electrically connected to the second conductive portion 610 of the patterned conductive layer 606. In one or more embodiments, the feedthrough pin 684 extends through the second conductive portion 610.

The conductive pads 604 can be manufactured separately from the header 666 and connected to the header using any suitable technique. In one or more embodiments, the conductive pads 604 can be integral with the header 666 and be formed as conductive posts that extend from the inner surface 668 of the header.

Any suitable technique can be utilized to form one or more of the embodiments of feedthrough assemblies described herein. For example, FIG. 19 is a flowchart of one method 700 of forming the feedthrough assembly 42 of FIGS. 1-11. Although described in regard to feedthrough assembly 42, the method 700 can be utilized to form any suitable feedthrough assembly. At 702, one or more test pads 82 can be disposed on the first major surface 74 of the test fanout layer 72 using any suitable technique. For example, a conductive layer can be disposed on the first major surface 74 and patterned, e.g., by etching the conductive layer through a mask. In one or more embodiments, the test via 80 can be disposed in the test fanout layer 72 such that it extends between the first major surface 74 and the second major surface 76, and the test pad 82 can be electrically connected to the test via using any suitable technique. At 704, the first major surface 74 of the test fanout layer 72 can be disposed such that it faces the inner surface 68 of the header 66 using any suitable technique. Further the test fanout layer 72 is disposed such that at least a portion of one or more of the test pads 82 is disposed between the outer surface 70 of the header 66 and the perimeter 78 of the test fanout layer when viewed in the plane parallel to the first major surface of the test fanout layer, i.e., the at least a portion of the test pad is exposed.

At 706, the header 66 can be electrically connected to the test fanout layer 72 using any suitable technique. For example, a patterned conductive layer (e.g., patterned conductive layer 606 of FIG. 18) can be disposed on the first major surface 74 of the test fanout layer 72, where the patterned conductive layer includes a first conductive portion (e.g., first conductive portion 608 of FIG. 18) and a second conductive portion (e.g., second conductive portion 610 of FIG. 18). The header 66 can be connected to the first conductive portion and the feedthrough pin 84 can be electrically connected to the second conductive portion. In one or more embodiments, the electronic components 92 of the test fanout layer 72 can be disposed on or within the layer and electrically connected to at least one of first or second conductive portions of the patterned conductive layer.

In one or more embodiments, the header 66 can be mechanically and electrically connected to the test fanout layer 72 using any suitable technique. Further, the feedthrough pin 84 can be disposed within the header via 86 that extends through the header 66 at 708 using any suitable technique, where the feedthrough pin extends outward beyond the outer surface 70 of the header. At 710, the feedthrough pin 84 can be electrically connected to the test fanout layer 72 using any suitable technique. In one or more embodiments, a solder joint can be formed between the feedthrough pin 84 and metallized through hole 95. In one or more embodiments, solder can be disposed between the feedthrough pin 84 and the patterned conductive layer (e.g., patterned conductive layer 606 of FIG. 18). In one or more embodiments, the header 66 can be electrically connected to the test fanout layer 72 by disposing an adhesive layer (e.g., adhesive layer 202 of FIG. 14) between the inner surface 68 of the header and the first major surface 74 of the test fanout layer, and disposing solder (e.g., solder 204 of FIG. 14) between the conductive pad disposed on the inner surface of the header and the patterned conductive layer disposed on the test fanout layer. Further, in one or more embodiments, the header 66 can be electrically connected to the test fanout layer 72 by disposing an anisotropic conductive adhesive layer (e.g., anisotropic conductive adhesive layer 302 of FIG. 15) between the inner surface 68 of the header 66 and the test fanout layer.

The test pad 84 can be electrically connected to the electronic component 64 disposed on the substrate 54 of the first electronic layer 48 using any suitable technique. The substrate 54 of the first electronic layer 48 faces the second major surface 76 of the test fanout layer 72.

In one or more embodiments where the feedthrough assembly is a component of an implantable medical device, the header 66 can be connected to a first end of the housing 14 such that the electronic layers 40 (e.g., first electronic layer 48) is disposed within the housing. The power source (e.g., battery 30) can be electrically connected to the electronic layers 40 using any suitable technique.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A feedthrough assembly comprising:
a header comprising an inner surface and an outer surface;
a test fanout layer electrically connected to the header, the test fanout layer comprising:
a first major surface, a second major surface, and a perimeter, wherein the first major surface of the test fanout layer faces the inner surface of the header;
a test via extending between the first major surface and the second major surface of the test fanout layer; and
a test pad disposed on the first major surface of the test fanout layer and electrically connected to the test via, wherein at least a portion of the test pad is disposed between the outer surface of the header and the perimeter of the test fanout layer as viewed in a plane parallel to the first major surface of the test fanout layer such that the at least a portion of the test pad is exposed.

2. The assembly of claim 1, further comprising a first feedthrough pin disposed within a first header via that extends through the header, wherein the first feedthrough pin extends outward beyond the outer surface of the header.

3. The assembly of claim 2, further comprising a redistribution layer disposed between the header and the test fanout layer, wherein the test fanout layer and the first feedthrough pin are electrically connected to the header utilizing the redistribution layer.

4. The assembly of claim 1, further comprising an electronic component disposed on or within the test fanout layer and electrically connected to the header.

5. The assembly of claim 1, wherein a post disposed on the inner surface of the header is electrically connected to a metallized through hole of the test fanout layer.

6. The assembly of claim 1, wherein the header is electrically connected to the test fanout layer by a patterned conductive layer disposed on the first major surface of the test fanout layer, wherein the patterned conductive layer comprises a first conductive portion and a second conductive portion electrically isolated from the first conductive portion.

7. The assembly of claim 1, further comprising a plurality of test pads disposed on the test fanout layer, wherein each test pad of the plurality of test pads is electrically connected to a test via that extends between the first major surface and the second major surface of the test fanout layer.

8. The assembly of claim 1, wherein the assembly extends along a longitudinal axis such that the first and second major surfaces of the test fanout layer are substantially orthogonal to the longitudinal axis, and further wherein a normal to the test pad is substantially parallel to the longitudinal axis.

9. An electronics module comprising:

an electronic layer comprising a substrate and an electronic component disposed on the substrate; and a feedthrough assembly electrically connected to the electronic layer, the feedthrough assembly comprising:

a header comprising an inner surface and an outer surface;

a test fanout layer electrically connected to the header, the test fanout layer comprising:

a first major surface, a second major surface, and a perimeter, wherein the first major surface of the test fanout layer faces the inner surface of the header; and a test pad disposed on the first major surface of the test fanout layer and electrically connected to the electronic component of the electronic layer, wherein at least a portion of the test pad is disposed between the outer surface of the header and the perimeter of the test fanout layer as viewed in a plane parallel to the first major surface of the test fanout layer such that the at least a portion of the test pad is exposed.

10. The module of claim 9, further comprising a test via that extends between the first major surface and the second major surface of the test fanout layer, wherein the test via electrically connects the test pad to the electronic component.

11. The module of claim 10, wherein the test fanout layer further comprises a second test pad disposed on the first major surface of the test fanout layer, wherein at least a portion of the second test pad is disposed between the outer surface of the header and the perimeter of the test fanout layer as viewed in a plane parallel to the first major surface of the test fanout layer such that the at least a portion of the second test pad is exposed.

12. The module of claim 11, wherein the second test pad is electrically connected to a second electronic component of the electronic layer.

13. The module of claim 12, wherein the test via is a first test via, the module further comprising a second test via that extends between the first major surface and the second major surface of the test fanout layer, wherein the second test via electrically connects the second test pad to the second electronic component of the electronic layer.

14. The module of claim 9, wherein the feedthrough assembly further comprises a feedthrough pin disposed within a via that extends through the header, wherein the feedthrough pin extends beyond the outer surface of the header.

15. An implantable medical device comprising the electronics module of claim 9.

16. A method comprising:

disposing a test pad on a first major surface of a test fanout layer;

disposing the first major surface of the test fanout layer such that it faces an inner surface of a header and such that at least a portion of the test pad is disposed between an outer surface of the header and a perimeter of the test fanout layer when viewed in a plane parallel to the first major surface of the test fanout layer, wherein the at least a portion of the test pad is exposed;

electrically connecting the header to the test fanout layer;

disposing a feedthrough pin within a header via that extends through the header, wherein the feedthrough pin extends outward beyond an outer surface of the header;

electrically connecting the feedthrough pin to the test fanout layer; and electrically connecting the test pad to an electronic component disposed on a substrate of an electronic layer disposed such that it faces a second major surface of the test fanout layer.

17. The method of claim 16, further comprising:

disposing a test via in the test fanout layer such that it extends between the first major surface and the second major surface of the test fanout layer; and electrically connecting the test pad to the test via.

18. The method of claim 16, further comprising disposing one or more electronic components on or within the test fanout layer.

19. The method of claim 16, further comprising disposing a patterned conductive layer on the first major surface of the test fanout layer, wherein the patterned conductive layer comprises a first conductive portion and a second conductive portion.

20. The method of claim 16, wherein electrically connecting the header to the test fanout layer comprises:

disposing an adhesive layer between the inner surface of the header and the first major surface of test fanout layer; and disposing solder between a conductive pad disposed on the inner surface of the header and the patterned conductive layer.

* * * * *